US012352776B2

(12) United States Patent
Laput et al.

(10) Patent No.: US 12,352,776 B2
(45) Date of Patent: Jul. 8, 2025

(54) METHODS AND APPARATUS FOR DETECTING INDIVIDUAL HEALTH RELATED EVENTS

(71) Applicant: Apple Inc., Cupertino, CA (US)

(72) Inventors: Gierad Laput, Pittsburgh, PA (US); Jared LeVan Zerbe, Woodside, CA (US); William C. Athas, San Jose, CA (US); Andreas Edgar Schobel, San Francisco, CA (US); Shawn R. Scully, Seattle, WA (US); Brian H. Tsang, Belmont, CA (US); Kevin Lynch, Woodside, CA (US); Charles Maalouf, Seattle, WA (US); Shiwen Zhao, Bothell, WA (US)

(73) Assignee: Apple Inc., Cupertino, CA (US)

( * ) Notice: Subject to any disclaimer, the term of this patent is extended or adjusted under 35 U.S.C. 154(b) by 10 days.

(21) Appl. No.: 18/158,412

(22) Filed: Jan. 23, 2023

(65) Prior Publication Data
US 2023/0160922 A1 May 25, 2023

Related U.S. Application Data

(63) Continuation of application No. 16/994,524, filed on Aug. 14, 2020, now Pat. No. 11,639,944.
(Continued)

(51) Int. Cl.
G01J 1/42 (2006.01)
G01P 13/00 (2006.01)
(Continued)

(52) U.S. Cl.
CPC ............ *G01P 15/18* (2013.01); *G01J 1/4204* (2013.01); *G01P 13/00* (2013.01); *G10L 25/51* (2013.01); *H04R 1/08* (2013.01)

(58) Field of Classification Search
CPC ........ G01P 15/18; G01P 13/00; G01J 1/4204; G10L 25/51; H04R 1/08
See application file for complete search history.

(56) References Cited

U.S. PATENT DOCUMENTS 8,758,262 B2 6/2014 Rhee et al.
9,373,242 B1 6/2016 Conrad et al.
(Continued)

FOREIGN PATENT DOCUMENTS

CN 1598804 A 3/2005
CN 101796553 A 8/2010
(Continued)

OTHER PUBLICATIONS

Search Report received for Chinese Patent Application No. 202010839719.X, mailed on Dec. 5, 2022, 5 pages (2 Pages of English Translation and 3 Pages of Official Copy).
(Continued)

Primary Examiner — Manuel A Rivera Vargas
(74) Attorney, Agent, or Firm — Kubota & Basol LLP

(57) ABSTRACT

Individual health related events (e.g., handwashing events) can be detected based on multiple sensors including motion and audio sensors. Detecting a qualifying handwashing event can include detecting a qualifying scrubbing event based on motion data (e.g., accelerometer data) and a qualifying rinsing event based on audio data. In some examples, power consumption can be reduced by implementing one or more power saving mitigations.

20 Claims, 8 Drawing Sheets

Related U.S. Application Data

(60) Provisional application No. 63/041,794, filed on Jun. 19, 2020, provisional application No. 62/891,944, filed on Aug. 26, 2019.

(51) Int. Cl.
  G01P 15/18  (2013.01)
  G10L 25/51  (2013.01)
  H04R 1/08  (2006.01)

(56) References Cited

U.S. PATENT DOCUMENTS

| | | | |
|---|---|---|---|
| 2003/0009703 | A1 | 1/2003 | Oshima et al. |
| 2008/0094077 | A1 | 4/2008 | Philipp |
| 2008/0303658 | A1 | 12/2008 | Melker et al. |
| 2009/0195385 | A1 | 8/2009 | Huang et al. |
| 2010/0073162 | A1 | 3/2010 | Johnson et al. |
| 2012/0002510 | A1 | 1/2012 | Berman, Jr. |
| 2012/0212344 | A1 | 8/2012 | Forsberg et al. |
| 2013/0033376 | A1 | 2/2013 | Seyed et al. |
| 2015/0127365 | A1 | 5/2015 | Rizvi et al. |
| 2016/0314683 | A1 | 10/2016 | Felch et al. |
| 2017/0239524 | A1 | 8/2017 | Lee et al. |
| 2017/0256155 | A1 | 9/2017 | Sengstaken, Jr. |
| 2018/0047277 | A1 | 2/2018 | Thyroff |
| 2018/0140204 | A1 | 5/2018 | Seo et al. |
| 2018/0293873 | A1* | 10/2018 | Liu .................. G16H 40/20 |
| 2019/0012898 | A1 | 1/2019 | Wittrup |
| 2019/0030277 | A1 | 1/2019 | Espi Maques et al. |
| 2019/0043337 | A1* | 2/2019 | Liu .................. G16H 40/20 |
| 2019/0147375 | A1 | 5/2019 | Ghazi et al. |
| 2019/0228640 | A1 | 7/2019 | Freedman et al. |
| 2021/0063434 | A1 | 3/2021 | Laput et al. |
| 2022/0260668 | A1* | 8/2022 | Yap .................. G01S 5/0295 |

FOREIGN PATENT DOCUMENTS

| | | |
|---|---|---|
| CN | 108078561 A | 5/2018 |
| CN | 108701495 A | 10/2018 |
| CN | 109427333 A | 3/2019 |
| CN | 109891032 A | 6/2019 |
| WO | 2008/028105 A2 | 3/2008 |
| WO | 2008/154494 A1 | 12/2008 |
| WO | 2014/015378 A1 | 1/2014 |
| WO | 2019/020977 A1 | 1/2019 |

OTHER PUBLICATIONS

Corrected Notice of Allowance received for U.S. Appl. No. 16/994,524, mailed on Feb. 2, 2023, 2 pages.

Intelligent Hand Hygiene Support, Stanford Partnership in AI-Assisted Care, Available online at: <https://aicare.stanford.edu/projects/hand_hygiene/>, Accessed on Aug. 25, 2020, 13 pages.

Non-Final Office Action received for U.S. Appl. No. 16/994,524, mailed on Mar. 30, 2022, 5 pages.

Notice of Allowance received for U.S. Appl. No. 16/994,524, mailed on Aug. 24, 2022, 7 pages.

Search Report received for Chinese Patent Application No. 202010839719.X, mailed on Jan. 17, 2022, 6 pages (3 pages of English Translation and 3 pages of Official Copy).

Supplemental Notice of Allowance received for U.S. Appl. No. 16/994,524 , mailed on Nov. 23, 2022, 2 pages.

Chatrzarrin, Hanieh, "Feature Extraction for the Differentiation of Dry and Wet Cough Sounds", Carleton University, Ottawa-Carleton Institute for Biomedical Engineering (OCIBME), ISBN: 978-0-494-83057-4, Sep. 2011, 144 pages.

Liaqat et al., "Challenges with Real-World Smartwatch based Audio Monitoring", WearSys'18, Munich, Germany, Jun. 10, 2018, 6 pages.

Notice of Allowance received for U.S. Appl. No. 16/994,524, mailed on Mar. 2, 2023, 9 pages.

Search Report received for Chinese Patent Application No. 202010839719.X, mailed on Dec. 26, 2023, 7 pages (2 pages of English Translation and 5 pages of Official Copy).

Chaoqun, Feng, "Hand Hygiene Status and Nursing Intervention of Nursing Assistants in Pension Institutions", Health Education and Health Promotion, vol. 14, No. 1, Feb. 20, 2019, pp. 64-66 (1 page of English Abstract, 2 pages of Official Copy). See attached Communication 37 CFR § 1.98(a)(3).

Hoey et al., "Automated Handwashing Assistance for Persons with Dementia Using Video and a Partially Observable Markov Decision Process", Computer Vision and Image Understanding, vol. 114, Feb. 1, 2010, pp. 503-519.

Snoek et al., "Automatic Segmentation of Video to Aid the Study of Faucet Usability for Older Adults", IEEE Computer Society Conference on Computer Vision and Pattern Recognition, Jun. 13-18, 2010, pp. 63-70.

Yongchang, Zhang, "Management of Hand Hygiene Compliance Based on Internet of Things Sensor", Wireless Internet Technology, Issue 24, Dec. 2018, 3 pages (1 page of English Abstract, 2 pages of Official Copy). See attached Communication 37 CFR § 1.98(a)(3).

* cited by examiner

METHODS AND APPARATUS FOR DETECTING INDIVIDUAL HEALTH RELATED EVENTS

CROSS-REFERENCE TO RELATED APPLICATIONS

This application is a continuation of U.S. patent application Ser. No. 16/994,524, filed Aug. 14, 2020, and published on Mar. 4, 2021 as U.S. Publication No. 2021-0063434, which claims the benefit under 35 U.S.C. 119(e) of U.S. Provisional Patent Application No. 62/891,944, filed Aug. 26, 2019, and of U.S. Provisional Patent Application No. 63/041,794, filed Jun. 19, 2020, which are incorporated by reference herein in their entireties for all purposes.

FIELD

This relates generally to methods and apparatus for detecting individual health related events, and more particularly, to methods and apparatus for detecting individual health related events based on multiple sensors including motion and audio sensors.

BACKGROUND

Washing hands can prevent illness for a person washing and prevent the spread of illness to others. Handwashing practices, however, vary greatly. It may be useful to have an electronic device detect handwashing events.

SUMMARY

This relates to detecting individual health related events (e.g., handwashing events) based on multiple sensors including motion and audio sensors. Detecting a qualifying handwashing event can include detecting a qualifying scrubbing event based on motion data (e.g., accelerometer data) and a qualifying rinsing event based on audio data. In some examples, power consumption can be reduced by implementing one or more power saving mitigations. In some examples, acquiring and processing motion data can be used to trigger the acquisition and/or processing of audio data. In some examples, processing of motion data by a low-power processor can be used to trigger the acquisition and/or processing of audio data by another processor (e.g., a host processor). In some examples, the quality of the acquired data and/or the quality of the processing of the acquired data streams can be changed based on one or more triggers. In some examples, the trigger(s) described herein can be dynamically adjusted (e.g., heightened to reduce processing/power consumption) based on one or more power-related states of the device.

DETAILED DESCRIPTION

Figure 1A:
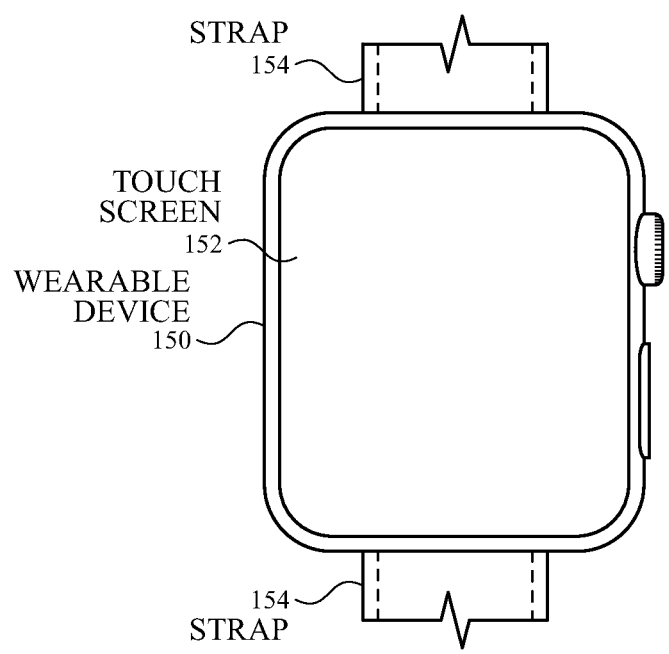
FIGS. 1A-1B illustrate an example system for detecting individual health related events based on one or more sensors according to examples of the disclosure.

In the following description of examples, reference is made to the accompanying drawings which form a part hereof, and in which it is shown by way of illustration specific examples that can be practiced. It is to be understood that other examples can be used and structural changes can be made without departing from the scope of the disclosed examples.

This relates to detecting individual health related events (e.g., handwashing events) based on multiple sensors including motion and audio sensors. Detecting a qualifying handwashing event can include detecting a qualifying scrubbing event based on motion data (e.g., accelerometer data) and a qualifying rinsing event based on audio data. In some examples, the data acquisition (of motion and audio data) and processing of the data can be "always on" (e.g., operating continuously or at regular intervals) to provide direct feedback regarding detection of handwashing events. In some examples, power consumption can be reduced by implementing one or more power saving mitigations. The power saving mitigations can include delaying data acquisition, processing, and/or reporting of feedback regarding detection of handwashing events. In some examples, acquiring and processing motion data can be used to trigger the acquisition and/or processing of audio data. In some examples, processing of motion data by a low-power processor can be used to trigger the acquisition and/or processing of audio data by another processor (e.g., a host processor). In some examples, the quality of the acquired data and/or the quality of the processing of the acquired data streams can be changed based on one or more triggers. In some examples, the trigger(s) described herein can be dynamically adjusted (e.g., heightened to reduce processing/power consumption) based on one or more power-related states of the device.

As discussed herein, detecting individual health related events can include a detecting a handwashing event (e.g., detecting inputs the system considers to be washing hands). The handwashing event can include a scrubbing event (e.g., detecting inputs the system considers to be scrubbing hands together) and a rinsing event (e.g., detecting inputs the system considers to be rinsing of the hands with water). As used herein, qualifying events refer to events that meet one or more criteria set for the system. For example, detecting a qualifying scrubbing event based on (e.g., using) motion data can include detecting motion data meeting one or more criteria optionally including a duration criterion, an amplitude criterion, a speed criterion, etc. The one or more criteria can be set to differentiate between motion associated with scrubbing hands together from other motion (e.g., lifting a wrist, swinging arms, various exercises, sitting, typing, etc.). Likewise, detecting a qualifying rinsing event based on (e.g., using) audio data can include detecting audio data meeting one or more criteria optionally including a duration criterion, an amplitude criterion, a frequency content criterion, etc. The one or more criteria can be set to differentiate between audio associated with rinsing hands from other audio (e.g., environmental sounds, traffic, wind, etc.). In some examples, detecting a qualifying handwashing event can include meeting one or more criteria. The one or more criteria can including detecting a qualifying rinsing event within a threshold period of time (e.g., within 30 second, within 1 minute, etc.) of detecting a qualifying scrubbing event.

Figure 1B:
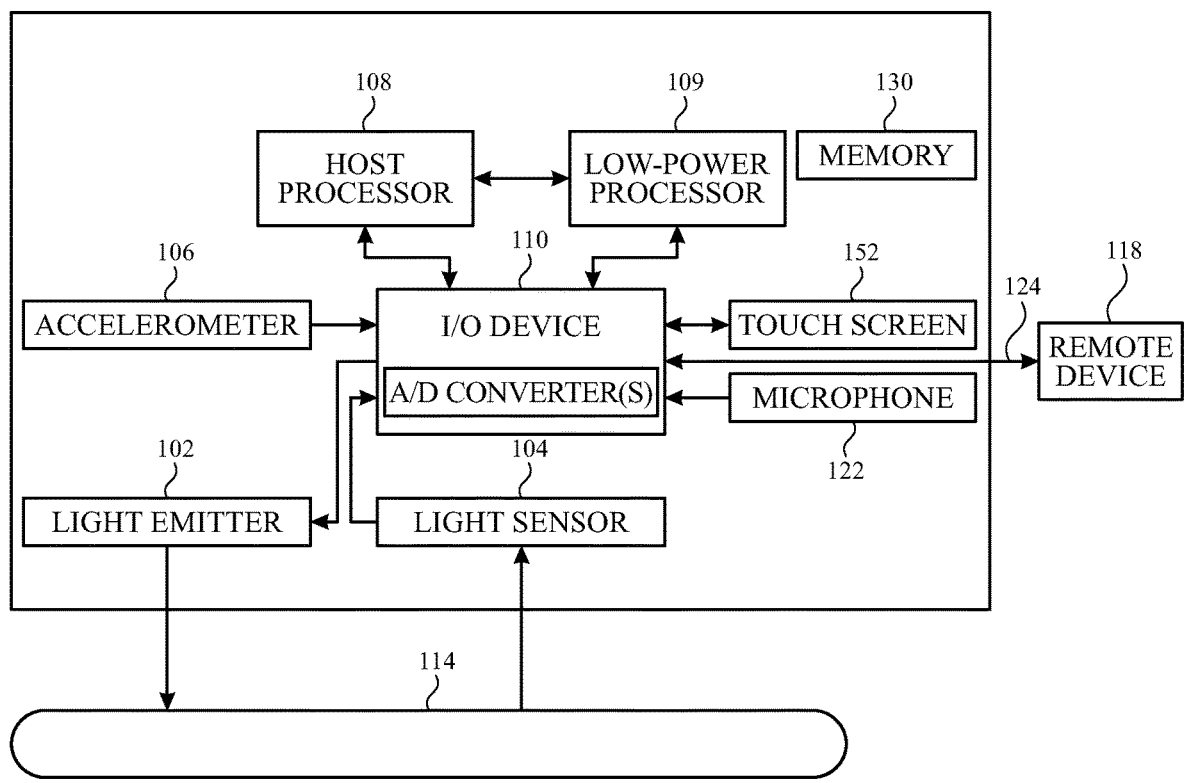

FIGS. 1A-1B illustrate an example system for detecting individual health related events based on one or more sensors according to examples of the disclosure. FIG. 1A illustrates an example wearable device 150 (e.g., a watch) that can include an integrated touch screen 152, one or more sensors 160 (e.g., accelerometer, microphone, light sensor, etc.), and processing circuitry programmed to detect individual health related events (e.g., handwashing events) according to examples of the disclosure. Wearable device 150 can be attached to a user using strap 154, for example. It is understood that although wearable device 150 includes a touch screen, the detection of individual health related events described herein can be applied to a device without or without a touch-sensitive or a non-touch-sensitive display. It is understood that wearable device 150 illustrated in FIG. 1A is one example of a wearable device, but the detection of individual health related events can be implemented in part or entirely in other wearable devices (e.g., ring, smart band, health band, finger-cuff, wrist-cuff, glove, etc.).

FIG. 1B illustrates an example block diagram 100 of a system for detecting individual health related events, including example wearable device 150 of FIG. 1A, according to examples of the disclosure. Block diagram 100 can include an electronic device corresponding to wearable device 150. Wearable device 150 can include a light sensing system including, for example, one or more light emitters 102 and one or more light sensors 104. Wearable device 150 can include a motion sensing system including, for example, one or more accelerometers 106. Wearable device 150 can include an audio sensing system, for example, including a microphone 122. Wearable device 150 can also include touch screen 152. Processing circuitry in wearable device 150, optionally including host processor 108 and low-power processor 109, can be programmed to operate and/or process data from the light sensing system, motion sensing system, audio sensing system and touch screen 152. In some examples, the light sensing system, the motion sensing system, the audio sensing system and/or the touch screen can be coupled to the processing circuitry via an input/output (I/O) device 110. I/O device 110 can, in some examples, include one or more analog-to-digital converters (ADCs) to convert analog signals from the light sensing system, the motion sensing system and/or the audio sensing systems into digital signals for processing by processing circuitry.

These above-described components of block diagram 100 can be incorporated within wearable device 150 that can be attached to a user via a strap 154, or otherwise be secured to a user's skin (a user's wrist, for example), or otherwise attached to an article of clothing worn by the user (a user's shirt sleeve, for example). The light emitter(s) 102 and light sensor(s) 104 can be positioned proximate to a user's skin such that a portion of the light from one or more light emitters 102 (e.g., one or more light emitting diodes) can be absorbed by the skin 114, vasculature, and/or blood, among other possibilities, and a portion can be reflected back to one or more light sensors 104 (e.g., photodiodes). For example, the light sensor(s) 104 can convert this light into an electrical signal indicative of the intensity of reflected light. Light sensor(s) 104 can be co-located with light emitter(s) 102, in some examples (e.g., on the back of wearable device 150).

The signals from the light sensor(s) 104 can be photoplethysmogram (PPG) signals that can include indications of physiological conditions including heart rate, electrocardiogram, blood oxygenation, etc.

The motion sensing system, represented in FIG. 1B by accelerometer 106, can provide acceleration output signals indicative of acceleration due to movements of the user ("acceleration data" or more generally "motion data"). For example, wearable device 150 can be worn on a user's wrist, and the accelerometer output signals can be indicative of scrubbing motion while washing hands. In other examples, the accelerometer output signals can be indicative of the other arm or hand movements (e.g., arm swings) or gait (e.g., foot strike rate) of the user. In some examples, the accelerometer can be a three-axis accelerometer providing three-dimensional acceleration outputs (e.g., three channels of acceleration outputs). Although primarily described herein as an accelerometer and acceleration data, it should be understood that other sensors can be used to acquire or infer motion data (e.g., gyroscopes, inertial measurement units (IMUs), position sensors, etc.). The motion data from the accelerometer (and/or other sensors) can be processed for detection of qualifying scrubbing events.

The audio sensing system, represented in FIG. 1B by microphone(s) 122, can provide audio output signals ("audio data"). For example, wearable device 150 can be worn on a user's wrist and the audio signals can be indicative of rinsing while washing hands.

The analog outputs of the light sensing system (from light sensor(s) 104), the motion sensing system (from accelerometer(s) 106) and/or from audio sensing system (from microphone(s) 122) can be converted to digital form using ADCs (e.g., in I/O device 110). In some examples, the digitized data can be stored in memory 130 in wearable device 150. Processing circuitry, including host processor 108 and/or low-power processor 109, can receive the digitized data from one or more of these sensors (or from memory 130) and can process the data. In some examples, as described herein, the motion data (e.g., from accelerometer 106) and the audio data (e.g., from microphone 122) can be processed by the processing circuitry to identify individual health related events. The individual health related events can include handwashing events.

I/O device 110 can be coupled to a remote device 118 via a wired or wireless communication link 124. The remote device 118 can be any wearable or non-wearable device including mobile telephone, tablet computer, personal computer, portable media player, data server etc. In some examples, the remote device 118 can receive information regarding the detection of an individual health event by processing circuitry of wearable device 150.

Additionally, in some examples, one or more of the sensors and some or all of the processing to detect individual health related events can be implemented in one or more remote devices including wearable or non-wearable devices. For example, one or more of the sensors may be implemented in a second wearable or non-wearable device. In some examples, the accelerometer 106 of wearable device 150 can be used to gather motion data and a microphone in a mobile telephone (e.g., remote device 118) in communication with wearable device 150 can be used to gather audio data. Data streams from the one or more sensors from the wearable device(s) and/or from a non-wearable device(s) may be processed by processing circuitry in the wearable device(s) and/or non-wearable device(s). For example, one or more data streams (motion data, audio data) can be communicated via wired or wireless channels to processing circuitry in a wearable or non-wearable device. For example, motion data and/or audio data can be communicated from wearable device 150 to remote device 118, and processing circuitry in remote device 118 can be used to process the data streams to detect individual health related events. In some examples, some of the processing described herein can be performed by processing circuitry in the wearable device and/or some of the processing can be performed by processing circuitry in the non-wearable device.

Figure 2:
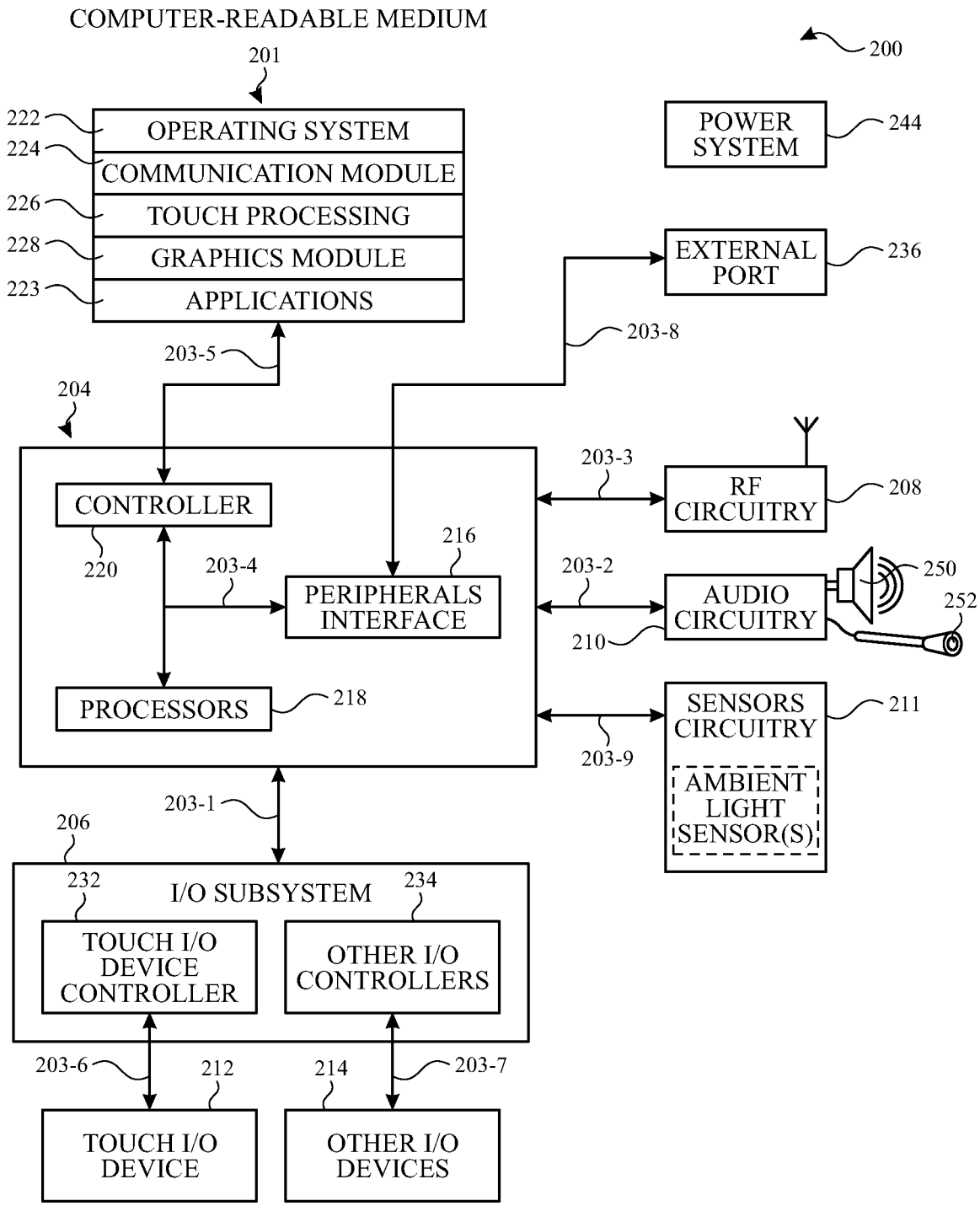
FIG. 2 illustrates a block diagram of an example computing system that can be used for detecting individual health related events according to examples of the disclosure.

FIG. 2 illustrates a block diagram of an example computing system 200 that can be used for detecting individual health related events according to examples of the disclosure. Computing system 200 can correspond to circuitry in the wearable and non-wearable devices described herein. The block diagram can generally include a computer-readable medium 201 (e.g., including a memory hierarchy, including but not limited to cache, main memory and secondary memory), processing circuitry 204, I/O subsystem 206, radio frequency (RF) circuitry 208, audio circuitry 210, and sensors circuitry 211. These components can be coupled by one or more communication buses or signal lines 203.

RF circuitry 208 can be used to send and receive information over a wireless link or network to one or more other devices (e.g., to communicate audio and/or motion data between devices) and includes well-known circuitry for performing this function. RF circuitry 208 and audio circuitry 210 can be coupled to processing circuitry 204 via peripherals interface 216 (e.g., corresponding to I/O device 110 in FIG. 1B). Peripherals interface 216 can include various known components for establishing and maintaining communication between peripherals and processing circuitry 204.

Audio circuitry 210 can be coupled to audio speaker 250 and microphone 252 (e.g., corresponding to microphone 122 in FIG. 1B) and can include known circuitry for processing voice signals received from peripherals interface 216 to enable a user to communicate in real-time with other users. In some examples, audio circuitry 210 can include a headphone jack (not shown). Sensors circuitry 211 can be coupled to various sensors including, but not limited to, one or more light emitting diodes (LEDs) or other light emitters (e.g., corresponding to light emitter(s) 102 in FIG. 1B), one or more photodiodes or other light sensors (e.g., corresponding to light sensor(s) 104 in FIG. 1B), one or more photothermal sensors, one or more magnetometers, one or more accelerometers (e.g., corresponding to accelerometer(s) 106 in FIG. 1B), one or more gyroscopes, one or more inertial measurement units (IMUs) or one or more IMU sub-components, one or more barometers, one or more compasses, one or more proximity sensors (e.g., infrared sensors), one or more cameras, one or more ambient light sensors, one or more thermometers, one or more global positioning system (GPS) sensors, and various system sensors which can sense remaining battery life, power consumption, processor speed, CPU load, and the like.

Peripherals interface 216 can couple the input and output peripherals of the computing system 200 to one or more processors 218 (e.g., corresponding to host processor 108 and/or low-power processor 109 in FIG. 1B) and one or more computer-readable media 201 via a controller 220. The one or more processors 218 communicate with the one or more computer-readable media 201 via the controller 220. The one more computer-readable media 201 can be any device or medium that can store code and/or data for use by the one or more processors 218.

Note that one or more of the functions described herein, including detecting individual health related events, can be performed by firmware stored in memory or program storage (e.g., medium 201) and executed by one or more processors (e.g., a low-power processor 109 and/or host processor 108). The firmware can also be stored and/or transported within any non-transitory computer-readable storage medium (e.g., computer-readable medium) for use by or in connection with an instruction execution system, apparatus, or device, such as a computer-based system, processor-containing system, or other system that can fetch the instructions from the instruction execution system, apparatus, or device and execute the instructions. In the context of this document, a "non-transitory computer-readable storage medium" can be any medium (excluding signals) that can contain or store the program for use by or in connection with the instruction execution system, apparatus, or device. The computer-readable storage medium can include, but is not limited to, an electronic, magnetic, optical, electromagnetic, infrared, or semiconductor system, apparatus or device, a portable computer diskette (magnetic), a random access memory (RAM) (magnetic), a read-only memory (ROM) (magnetic), an erasable programmable read-only memory (EPROM) (magnetic), a portable optical disc such a CD, CD-R, CD-RW, DVD, DVD-R, or DVD-RW, or flash memory such as compact flash cards, secured digital cards, USB memory devices, memory sticks, and the like.

The firmware can also be propagated within any transport medium for use by or in connection with an instruction execution system, apparatus, or device, such as a computer-based system, processor-containing system, or other system that can fetch the instructions from the instruction execution system, apparatus, or device and execute the instructions. In the context of this document, a "transport medium" can be any medium that can communicate, propagate or transport the program for use by or in connection with the instruction execution system, apparatus, or device. The transport medium can include, but is not limited to, an electronic, magnetic, optical, electromagnetic or infrared wired or wireless propagation medium. The transport medium can include a communications network, including but not limited to the Internet (also referred to as the World Wide Web), intranet (s), Local Area Networks (LANs), Wide Local Area Networks (WLANs), Storage Area Networks (SANs), Metropolitan Area Networks (MAN) and the like.

One or more processors 218 can run various software components stored in medium 201 to perform various functions for computing system 200. In some examples, the software components can include operating system 222, communication module (or set of instructions) 224, touch processing module (or set of instructions) 226, graphics module (or set of instructions) 228, and one or more applications (or set of instructions) 223. Each of these modules and above noted applications can correspond to a set of instructions for performing one or more functions described above and the methods described in this application (e.g., the computer-implemented methods and other information processing methods described herein). These modules (i.e., sets of instructions) need not be implemented as separate software programs, procedures or modules, and thus various subsets of these modules can be combined or otherwise re-arranged in various examples. In some examples, medium 201 can store a subset of the modules and data structures identified above. Furthermore, medium 201 can store additional modules and data structures not described above.

Operating system 222 can include various procedures, sets of instructions, software components and/or drivers for controlling and managing general system tasks (e.g., memory management, storage device control, power management, etc.) and facilitates communication between various hardware and software components. Communication module 224 can facilitate communication with other devices over one or more external ports 236 or via RF circuitry 208 and can include various software components for handling data received from RF circuitry 208 and/or external port 236. Graphics module 228 can include various known software components for rendering, animating and displaying graphical objects on a display surface. In examples in which touch I/O device 212 is a touch-sensitive display (e.g., a touch screen corresponding to touch screen 152 in FIG. 1B), graphics module 228 can include components for rendering, displaying, and animating objects on the touch-sensitive display.

Computing system 200 can also include the touch I/O device 212 (e.g., corresponding to touch screen 152) and/or other I/O devices 214 (e.g., corresponding to the light sensing system). Touch I/O device 212 can also incorporate a UI interface permitting a use to select among programming modes of displaying individual health event data (e.g., displaying handwashing performance, displaying a notification or other feedback regarding handwashing performance, etc.) when the touch I/O device is incorporated into wearable device 150 of FIG. 1B.

One or more applications 223 can include any applications installed on computing system 200, including without limitation, a browser, address book, contact list, email, instant messaging, word processing, keyboard emulation, widgets, JAVA-enabled applications, encryption, digital rights management, voice recognition, voice replication, location determination capability (such as that provided by the GPS), a music player, etc.

Touch processing module 226 can include various software components for performing various tasks associated with touch I/O device 212 including but not limited to receiving and processing touch input received from touch I/O device 212 via touch I/O device controller 232. The touch input can be used by computer programs stored in program storage 201 to perform actions that can include, but are not limited to, moving an object such as a cursor or pointer, scrolling or panning, adjusting control settings, opening a file or document, viewing a menu, making a selection, executing instructions, operating a peripheral device connected to the host device, answering a telephone call, placing a telephone call, terminating a telephone call, changing the volume or audio settings, storing information related to telephone communications such as addresses, frequently dialed numbers, received calls, missed calls, logging onto a computer or a computer network, permitting authorized individuals access to restricted areas of the computer or computer network, loading a user profile associated with a user's preferred arrangement of the computer desktop, permitting access to web content, launching a particular program, encrypting or decoding a message, and/or the like. The computer programs stored in program storage 201 can also cause the processing circuitry to perform the individual health related event detection described herein.

I/O subsystem 206 (corresponding to I/O device 110 of FIG. 1B) can be coupled to touch I/O device 212 and one or more other I/O devices 214 for controlling or performing various functions. Touch I/O device 212 can communicate with processing system 204 via touch I/O device controller 232, which can include various components for processing user touch input (e.g., scanning hardware). One or more other input controllers 234 can receive/send electrical signals from/to other I/O devices 214. Other I/O devices 214 can include physical buttons, dials, slider switches, sticks, keyboards, touch pads, additional display screens, or any combination thereof. If implemented as a touch screen, touch I/O device 212 can display visual output to the user in a GUI. The visual output can include text, graphics, video, and any combination thereof.

Some or all of the visual output can correspond to graphical user interface objects. Touch I/O device 212 can include a touch-sensitive surface that accepts touch input from the user. Touch I/O device 212 and touch screen controller 232 (along with any associated modules and/or sets of instructions in medium 201) can detect and track touches or proximity inputs (and any movement or release of the touch) on touch I/O device 212 and can convert the detected touch input into interaction with graphical objects, such as one or more user interface objects. In examples in which touch I/O device 212 is implemented as a touch screen, the user can directly interact with graphical user interface objects that can be displayed on the touch screen. Alternatively, in the case in which touch I/O device 212 is implemented as a touch device other than a touch screen (e.g., a touch pad), the user can indirectly interact with graphical user interface objects that can be displayed on a separate display screen implemented as I/O device 214.

Touch I/O device 212 can be analogous to the multi-touch sensing surface described in the following U.S. Pat. No. 6,323,846 (Westerman et al.), U.S. Pat. No. 6,570,557 (Westerman et al.), and/or U.S. Pat. No. 6,677,932 (Westerman), and/or U.S. Patent Publication 2002/0015024A1, each of which is incorporated by reference herein for all purposes. In examples in which touch I/O device 212 is a touch screen, the touch screen can use liquid crystal display (LCD) technology, light emitting polymer display (LPD) technology, organic LED (OLED), or organic electro luminescence (OEL), although other display technologies can be used in other examples.

Feedback can be provided by touch I/O device 212 (and/or by other I/O devices 214) based on the user's touch input as well as a state or states of what is being displayed and/or of the computing system. Feedback can be transmitted optically (e.g., light signal or displayed image), mechanically (e.g., haptic feedback, touch feedback, force feedback, or the like), electrically (e.g., electrical stimulation), olfactory, acoustically (e.g., beep or the like), or the like or any combination thereof and in a variable or non-variable manner.

Computing system 200 can also include power system 244 for powering the various hardware components and can include a power management system, one or more power sources, a recharging system, a power failure detection circuit, a power converter or inverter, a power status indicator and any other components typically associated with the generation, management and distribution of power in portable devices. In some examples, the power management system can adjust one or more aspects of the acquisition of data, processing of data and detecting individual health related events, as described in more detail herein.

In some examples, peripherals interface 216, one or more processors 218, and memory controller 220 of the processing circuitry 204 can be implemented on a single chip (an application specific integrated circuit) or on a single printed circuit board. In some other examples, they can be implemented on separate chips and/or across multiple printed circuit boards.

It should be understood that the block diagram shown in FIG. 2 can have more or fewer components than shown, or a different configuration of components. The various components shown in FIG. 2 can be implemented in hardware, software, firmware or any combination thereof, including one or more signal processing and/or application specific integrated circuits.

As discussed herein, detecting individual health related events can include a detecting a handwashing event. Detecting a qualifying handwashing event can include detecting a qualifying scrubbing event and a qualifying rinsing event. In some examples, handwashing events can be detected using one or more sensor data streams. In some examples, the sensor data streams can include motion data (e.g., acquired from an accelerometer) and audio data (e.g., acquired from a microphone). The motion data can be used to detect a qualifying scrubbing event and audio data can be used to detect a qualifying rinsing event. In some examples, motion and audio data can be used to detect the qualifying scrubbing event and/or the qualifying rinsing event. As used herein, qualifying events refer to events that meet one or more criteria. For example, detecting a qualifying scrubbing event based on motion data can include detecting motion data meeting one or more criteria optionally including a duration criterion, an amplitude criterion, a speed criterion, etc. The one or more criteria can be set to differentiate between motion associated with scrubbing hands together from other motion (e.g., lifting a wrist, swinging arms, various exercises, sitting, typing, etc.). Likewise, detecting a qualifying rinsing event based on audio data can include detecting audio data meeting one or more criteria optionally including a duration criterion, an amplitude criterion, a frequency content criterion, etc. The one or more criteria can be set to differentiate between audio associated with rinsing hands from other audio (e.g., environmental sounds, traffic, wind, etc.). In some examples, detecting a qualifying handwashing event can include meeting one or more criteria. The one or more criteria can including detecting a qualifying rinsing event within a threshold period of time (e.g., within 30 second, within 1 minute, etc.) of detecting a qualifying scrubbing event. Such criteria can be used to exclude false positive qualifying scrubbing events and/or false positive rinsing events that may not be indicative of a typical handwashing event.

Figure 3:
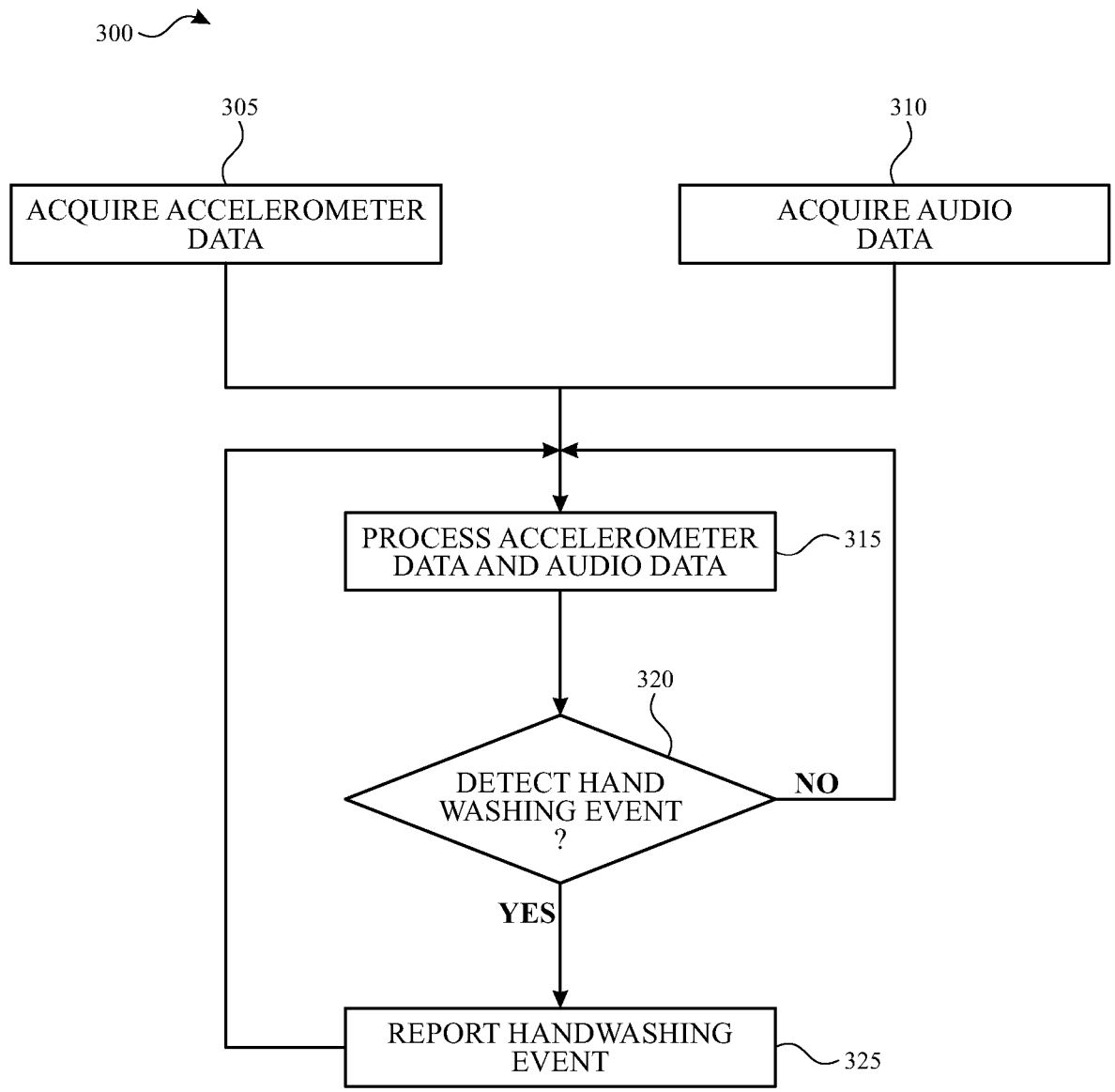
FIG. 3 illustrates an example process for detecting a handwashing event according to examples of the disclosure.

FIG. 3 illustrates an example process for detecting a handwashing event according to examples of the disclosure. Process 300 can include acquiring data from multiple sensors. For example, motion data (e.g., accelerometer data) and audio data can be acquired at 305 and 310, respectively. For example, accelerometer data can be acquired by accelerometer 106 and audio data can be acquired by microphone 122. The accelerometer data and audio data can be processed. For example, the processing can be performed by low-power processor 108 and/or host processor 109. The processing can include analysis of the accelerometer data to detect a qualifying scrubbing event (e.g., meeting the qualifying scrubbing event criteria) and analysis of the audio data to detect a qualifying rinsing event (e.g., meeting the qualifying rinsing event criteria). The processing can also include, for example, determining whether a qualifying handwashing event is detected at 320. When no qualifying handwashing event is detected, the processing of accelerometer and audio data can continue at 315 for subsequent accelerometer data and audio data (optionally, with some sleep or idle state for some duration before acquiring and/or processing subsequent accelerometer and/or audio data). When a qualifying handwashing event is detected, the handwashing event can be reported. When a qualifying handwashing event is reported, the acquisition and/or processing of accelerometer data and audio data can continue, in some examples, at 315 for subsequent accelerometer and audio data. The reported handwashing event can be used to track and/or log a user's handwashing performance. The user's handwashing performance can also be used to trigger feedback. In some examples, the detection of a handwashing event can start a count-down timer to help a user improve the effectiveness of handwashing.

Figure 4:
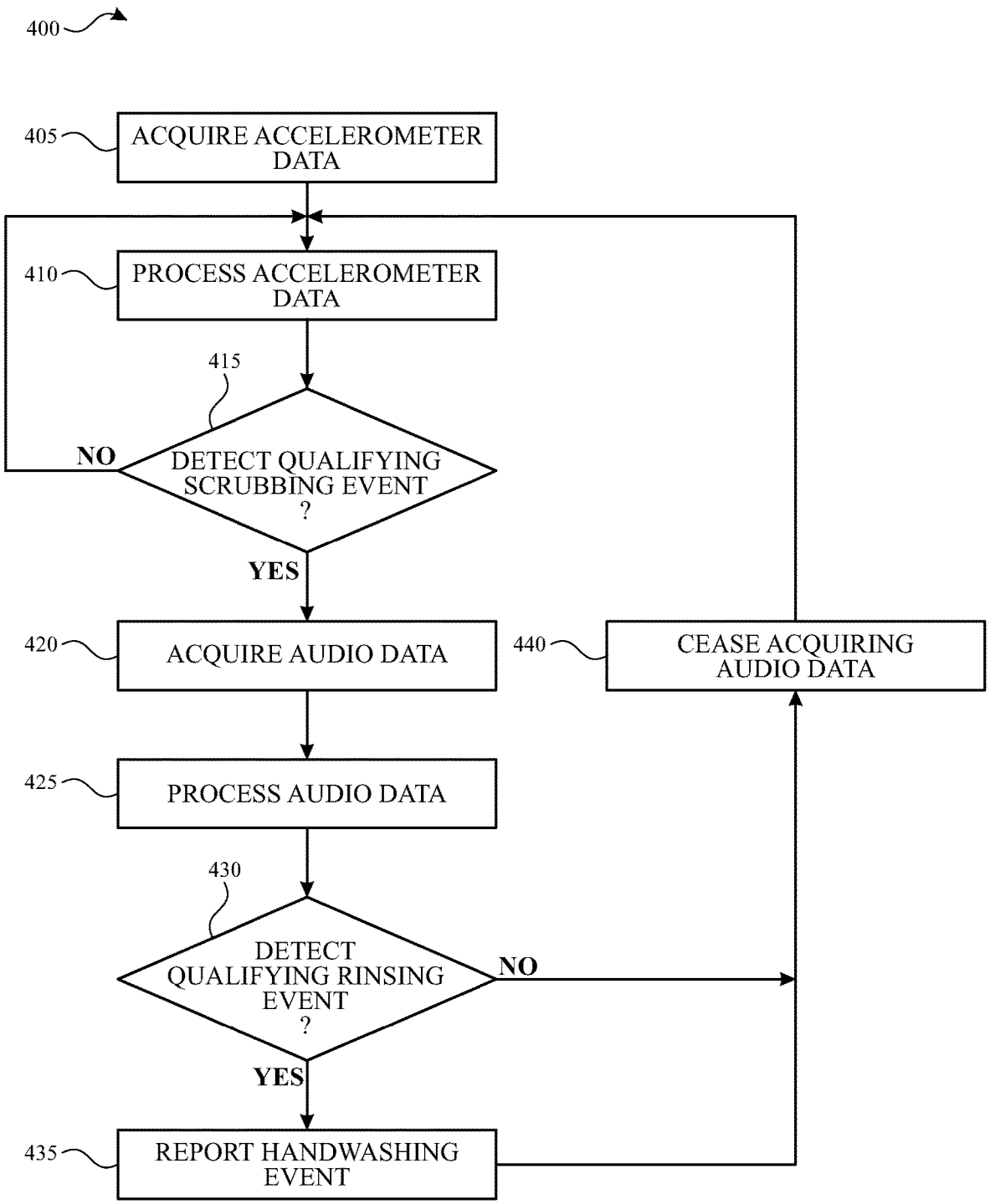
FIG. 4 illustrates another example process for detecting a handwashing event according to examples of the disclosure.

In some examples, power consumption can be reduced by sequencing the acquisition and/or processing of data. In some examples, processing of motion data can be used to trigger (or not trigger) the acquisition and/or processing of audio data to mitigate power consumption by the sensors and/or processing circuitry. FIG. 4 illustrates another example process for detecting a handwashing event according to examples of the disclosure. Process 400 can include acquiring data from multiple sensors. For example, motion data (e.g., accelerometer data) and audio data can be acquired. However, unlike in process 300, in process 400 the accelerometer data can be acquired at 405 (via accelerometer 106) without concurrently acquiring audio data prior to a trigger. At 410, the accelerometer data can be processed. For example, the processing can be performed by low-power processor 108 and/or host processor 109. The processing can include analysis of the accelerometer data to detect a qualifying scrubbing event (e.g., meeting the qualifying scrubbing event criteria). The processing can also include, for example, determining whether a qualifying scrubbing event is detected at 415. When no qualifying scrubbing event is detected, the acquisition and/or processing of accelerometer data can continue at 410 for subsequent accelerometer data (optionally, with some sleep or idle state for some duration before acquiring and/or processing subsequent accelerometer data). When a qualifying scrubbing event is detected, the audio data can be acquired at 425 (via microphone 122). At 425, the audio data can be processed. For example, the processing can be performed by low-power processor 108 and/or host processor 109. The processing can include analysis of the audio data to detect a qualifying rinsing event (e.g., meeting the qualifying rinsing event criteria). The processing can also include, for example, determining whether a qualifying rinsing event is detected at 430. When no qualifying rinsing event is detected, the system can cease acquiring audio data at 440, and the acquisition and/or processing of accelerometer data can continue at 410 for subsequent accelerometer data (optionally, with some sleep or idle state for some duration before acquiring and/or processing subsequent accelerometer data). When a qualifying rinsing event is detected, the handwashing event can be reported at 435. When a qualifying handwashing event is reported, the acquisition and/or processing of accelerometer data can continue, in some examples, at 410 for subsequent accelerometer data (optionally, with some sleep or idle state for some duration before acquiring and/or processing subsequent accelerometer data).

As shown in process 400, the acquisition and processing of audio data can be triggered by the detection of a qualifying scrubbing event. As a result, power can be saved by not acquiring audio data when unnecessary (e.g., by powering down the audio sensor and/or associated circuitry, such as ADCs)) and/or by not processing the audio data when there is no prior qualifying scrubbing event. In some examples, the audio data can be acquired concurrently with accelerometer data (e.g., as in process 300), but the processing of audio data can be triggered based on the detection of a qualifying scrubbing event (e.g., as in process 400). In some examples, the trigger for acquiring audio data and the trigger for processing audio data can be different triggers. For example, the acquisition of audio data can be triggered by detecting less than a qualifying scrubbing event (e.g., detecting motion that may meet some but not all of the qualifying scrubbing event criteria, such as detecting scrubbing motion meeting an amplitude criterion, but for less than the threshold duration), and the processing of audio data can be triggered by detecting the qualifying scrubbing event (e.g., detection motion that meets all of the qualifying scrubbing event criteria).

In some examples, processes 300 and 400 can be implemented in a low-power processor (e.g., low-power processor 109). In some examples, processes 300 and 400 can be implemented in a processor (e.g., host processor 108) that consumes more power than the low-power processor. It is understood that "low-power" processor described herein is lower power relative to another processor (e.g., a host processor). In some examples, a low-power processor may not include sufficient resources (e.g., memory, processing power, etc.) to implement all of processes 300 or 400. In some examples, power consumption can be improved by dividing the processing between two processors (e.g., between low-power processor 109 and host processor 108). In some examples, processing of motion data by the low-power processor can be used to trigger (or not trigger) the acquisition and/or processing of audio data by the host processor to mitigate power consumption and/or reduce processing requirements.

Figure 5:
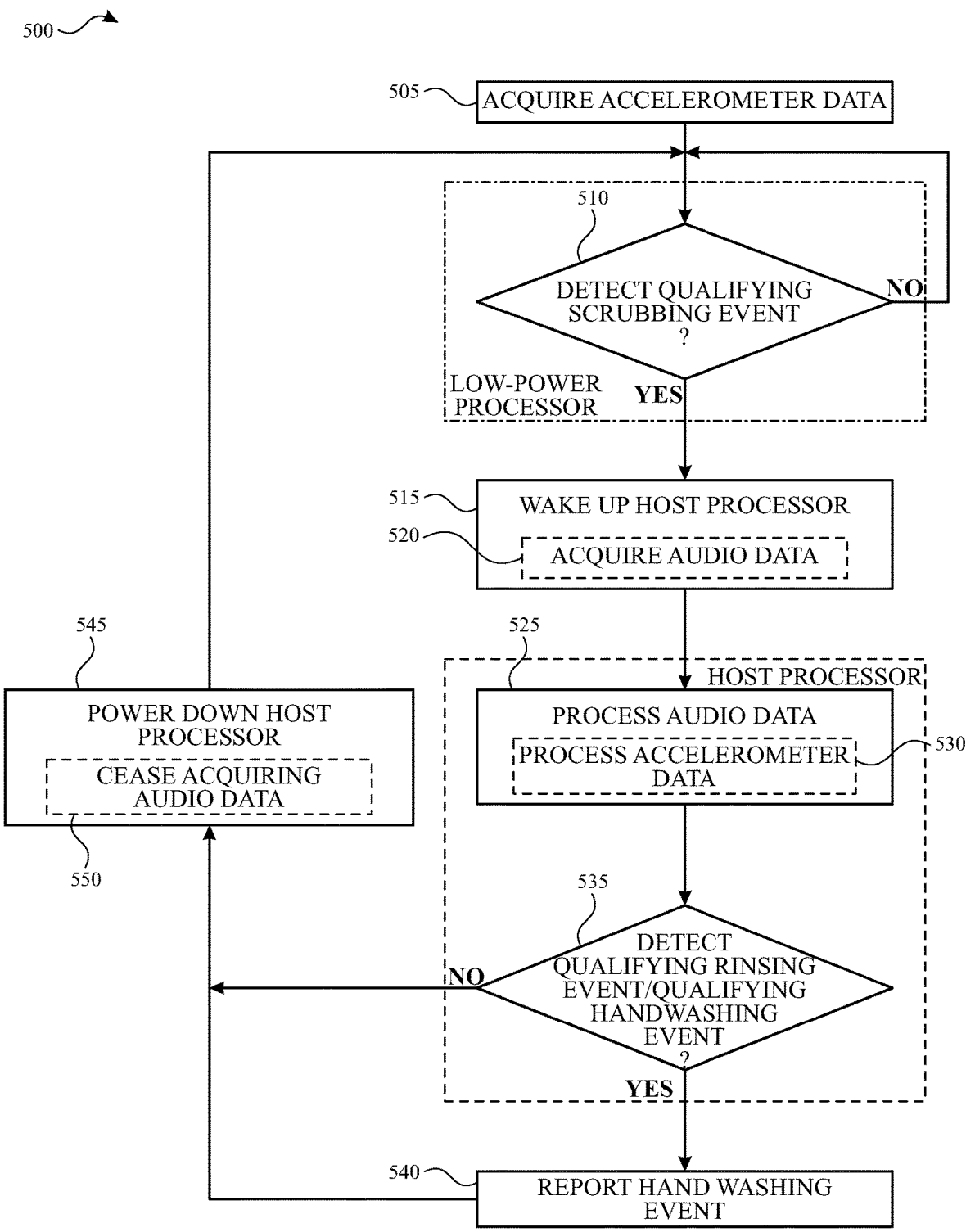
FIG. 5 illustrates another example process for detecting a handwashing event according to examples of the disclosure.

FIG. 5 illustrates another example process 500 for detecting a handwashing event according to examples of the disclosure. At 505, accelerometer data can be acquired (via accelerometer 106). At 510, the accelerometer data can be processed by a low-power processor (e.g., low-power processor 109) to detect a qualifying scrubbing event (or more generally, a qualifying motion event). When no qualifying scrubbing event is detected, the acquisition and/or processing of accelerometer data can continue at 505 for subsequent accelerometer data. When a qualifying scrubbing event is detected (e.g., in response to detecting the qualifying scrubbing event), another processor (e.g., host processor 108) can be woken up (activated) at 515. In some examples, the detection of a qualifying scrubbing event (or another trigger) can be used to acquire audio data at 520 (via microphone 122). In some examples, the acquisition of audio data can be acquired without an accelerometer-based trigger (e.g., as shown in process 300).

At 525, the host processor can process the audio data, and optionally, the host processor can also process the accelerometer data (530). The processing can include, at 535, detecting, a qualifying rinsing event (or more generally a qualifying audio event). When no qualifying rinsing event is detected, the system can power down (deactivate) the host processor at 545, and the acquisition and/or processing of accelerometer data by the low-power processor can continue at 505 for subsequent accelerometer data. In some examples, the system can cease acquiring audio data at 550 (and optionally power down the audio sensor) when no qualifying rinsing event is detected at 535. When a qualifying rinsing event is detected, the handwashing event can be reported at 540. In some examples, the host processor can also detect, at 535, a qualifying handwashing event prior to reporting the qualifying handwashing event. For example, the qualifying handwashing event can be detected based on detecting both the qualifying scrubbing event and qualifying rising event, and optionally based on other criteria (e.g., that the two events occur within a threshold period of time or occur at least partially concurrently). In some examples, the system can forgo processing to detect a qualifying handwashing event when no qualifying rinsing event is detected.

When a qualifying rinsing event and qualifying handwashing event is reported, the system can power down (deactivate) the host processor at 545 (and/or cease acquiring audio data at 550), and the acquisition and/or processing of accelerometer data can continue in the low-power processor, in some examples, at 505 for subsequent accelerometer data.

As described above, the accelerometer data can be processed (at 510) by a low-power processor to detect a qualifying scrubbing event (or more generally, a qualifying motion event), and then wake another processor (e.g., host-processor) at 515. The accelerometer data can also be processed by the host processor. In some examples, the processing at 510 can include applying a first accelerometer data model (e.g., a machine learning model) to the accelerometer data, and the processing at 530 can include applying a second accelerometer data model (e.g., a machine learning model). In some examples, the first accelerometer data model can be smaller (in terms of memory resources) and/or lower quality (in terms of processing accuracy) than the second accelerometer data model. In some examples, the first accelerometer data model can be used to make a first determination of a qualifying motion/scrubbing event. The second accelerometer data model can be used to refine the determination of a qualifying motion/scrubbing event. For example, the higher quality second accelerometer data model can provide better accuracy compared with the first accelerometer model due to its higher quality and its potential access to the accelerometer data for the duration of the wash/rinse and to the accelerometer data prior to triggering wake up of the second processor. In some examples, the threshold for detecting a qualifying motion/scrubbing event at 510 can be reduced compared with the threshold for detecting the qualifying scrubbing event at 530. For example, setting a low-bar trigger for waking up the processor can be useful to avoid missing potential handwashing events (e.g., a high escalation rate, low-power model that triggers the higher-accuracy, higher power model). In some examples, the output of the first accelerometer data model can be used as an input for the second accelerometer data model to refine the second accelerometer data model. In some examples, the output of the second accelerometer data model can be used to refine the first accelerometer data model. For example, the results of the subsequent labeling of scrubbing events by the second accelerometer data model using some of the data from the first accelerometer data model, can be used to improve the performance of the first accelerometer data model in detecting a qualifying scrubbing event.

Figure 6:
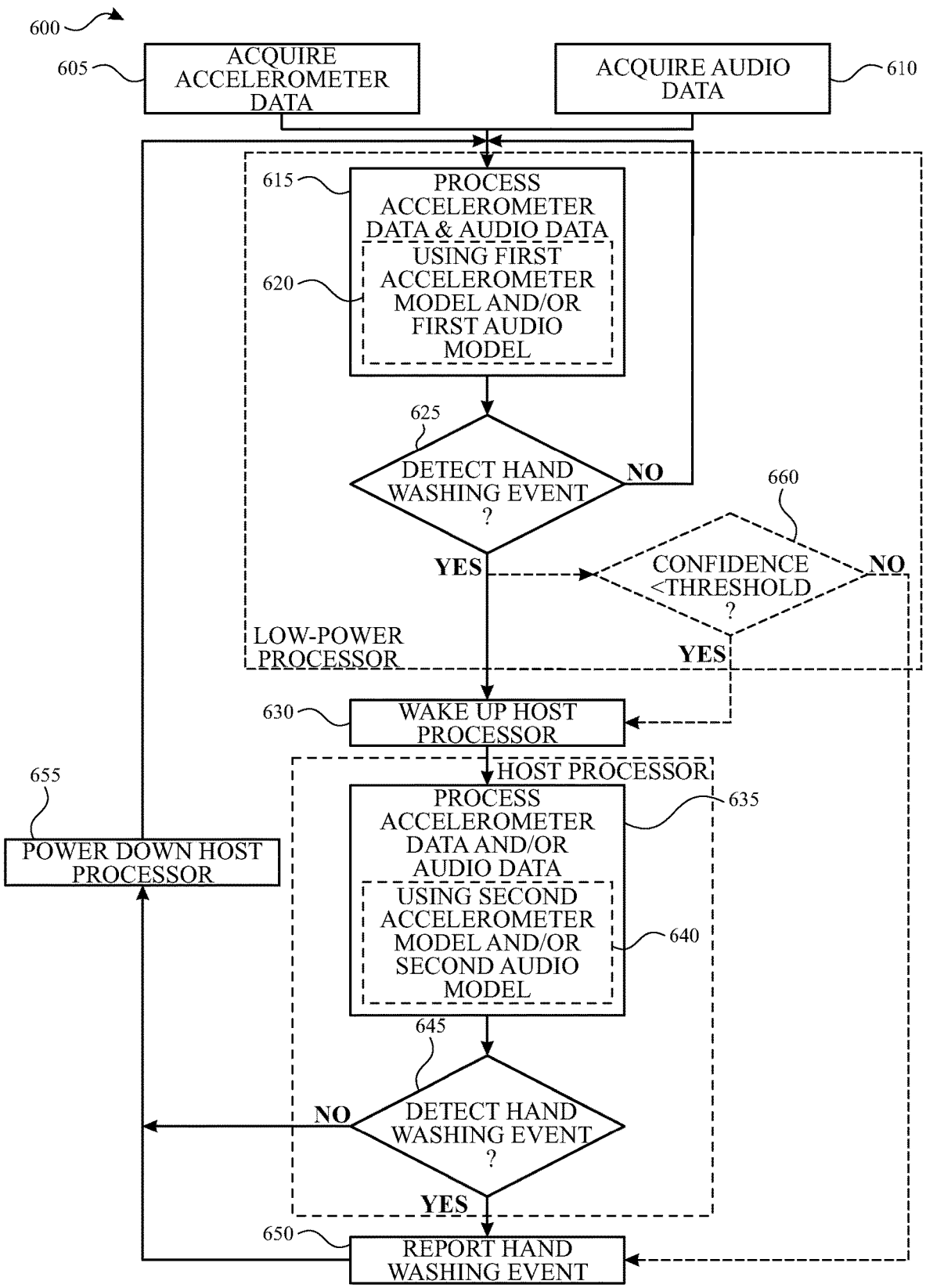
FIG. 6 illustrates another example process for detecting a handwashing event according to examples of the disclosure.

In some examples, power consumption can be improved by changing the quality of the acquired data streams and/or by changing the quality of the processing of the acquired data streams based on various triggers (to mitigate power consumption and/or reduce processing requirements). FIG. 6 illustrates another example process 600 for detecting a handwashing event according to examples of the disclosure. At 605 and 610, respectively, accelerometer data can be acquired (via accelerometer 106) and audio data can be acquired (via audio sensor 610). At 615, the accelerometer data and audio data can be processed by a low-power processor (e.g., low-power processor 109). The processing of accelerometer data can include using first accelerometer data processing and the processing of the audio data can include using first audio data processing. In some examples, the first accelerometer data processing can include applying a first accelerometer data model (e.g., a machine learning model) to the accelerometer data (620). In some examples, the first audio data processing can include applying a first audio data model (e.g., a machine learning model) to the audio data (620).

The processing can include detecting, at 625, a qualifying handwashing event (e.g., including detecting a qualifying scrubbing event based on the accelerometer data and detecting a qualifying rinsing event based on the audio data). When no qualifying handwashing event is detected, the acquisition and/or processing of accelerometer data can continue at 615 for subsequent accelerometer and/or audio data. When a qualifying handwashing event is detected, another processor (e.g., host processor 108) can be woken up (activated) at 630. Although the processing at 625 is described with reference to detecting a qualifying handwashing event, it should be understood that the processing can be sequenced such that accelerometer data can be processed first to detect a qualifying scrubbing event. When no qualifying scrubbing event is detected, the system can detect no handwashing event, and bypass the subsequent processing of audio data. Likewise, the processing can be sequenced such that the audio data can be processed in response to a qualifying scrubbing event. When no qualifying rinsing event is detected, the system can detect no handwashing event, and bypass subsequent processing to detect the occurrence of a handwashing event based on a qualifying scrubbing event and a qualified rinsing event.

At 635, the host processor can process the audio data and/or the accelerometer data. The processing can include, at 640, detecting, a qualifying handwashing event. The processing of accelerometer data can include using second accelerometer data processing and the processing of the audio data can include using second audio data processing. In some examples, the first and second processing of the accelerometer data and/or the audio data can be the same. In some examples, the first and second processing of the accelerometer data and/or the audio data can be different. In some examples, the second accelerometer data processing can include applying a second accelerometer data model (e.g., a machine learning model) to the accelerometer data (640). In some examples, the second accelerometer data model can be different than the first accelerometer data model. In some examples, the first accelerometer data model can be smaller (in terms of memory resources) and lower quality (in terms of processing accuracy) than the second accelerometer data model. In some examples, the second accelerometer model can be created using more training data than used to create the first accelerometer model. In some examples, the second audio data processing can include applying a second audio data model (e.g., a machine learning model) to the audio data (640). In some examples, the second audio data model can be different than the first audio data model. In some examples, the first audio data model can be smaller (in terms of memory resources) and lower quality (in terms of processing accuracy) than the second audio data model. In some examples, the second audio model can be created using more training data than used to create the first audio model. In some examples, the first and/or second audio data model can be based on a time-domain audio data. In some examples, the audio data model can be reduced in size/complexity by using a frequency domain representation of the audio data (e.g., using a Fourier transform such as a fast Fourier transform, or another transform). In some examples, the audio data model can be reduced in size/complexity by using a root mean square (RMS) representation of the audio data. In some examples, the audio data model can be reduced in size/complexity by using a Mel Frequency Cepstral (MFC) representation of the audio data (e.g., using MFC coefficients).

The processing can include detecting, at 645, a qualifying handwashing event (e.g., including detecting a qualifying scrubbing event based on the accelerometer data and detecting a qualifying rinsing event based on the audio data). The processing to detect the qualifying handwashing event by the host processor can be sequenced as described above for the processing by low-power process. When no qualifying rinsing event has been detected, the system can power down (deactivate) the host processor at 655, and the acquisition and/or processing of accelerometer data can continue at 615 for subsequent accelerometer and/or audio data. When a qualifying handwashing event has been detected, the handwashing event can be reported, at 650. When a qualifying handwashing event is reported, the system can power down (deactivate) the host processor at 655, and the acquisition and/or processing of accelerometer data and audio data can continue, in some examples, at 615 for subsequent accelerometer data and/or audio data.

Although FIG. 6 illustrates audio data and acceleration data acquired at least partially concurrently at 605 and 610, it should be understood that in some examples, the acquisition of audio data could be triggered (e.g., using an acceleration-based trigger) in a similar manner as described above with respect to FIG. 5. Additionally, it should be understood that in some examples, the quality of the data streams can be adjusted based on triggering conditions. For example, at 610, the acquisition of audio data can be performed such that the audio data has a first quality, and in response to detecting a qualifying scrubbing event based on the acceleration data, the acquisition of the audio data can be performed such that the audio data has a second quality greater than the first quality. For example, the sampling rate of the audio sensor (or a corresponding ADC) can be increased in response to a triggering event. In such a case, the audio data can be acquired continuously, with high quality audio acquired when most meaningful for detecting a subsequent qualifying rinsing event. In some examples, at 605, the acquisition of accelerometer data can be performed such that the accelerometer data has a first quality, and in response to detecting a triggering event (e.g., motion that satisfies some, but not all of the criteria for a qualifying scrubbing event) based on the acceleration data, the acquisition of the acceleration data can be performed such that the acceleration data has a second quality greater than the first quality. For example, the sampling rate of the accelerometer sensor (or a corresponding ADC) can be increased in response to a triggering event. In some examples, additional accelerometer channels can be used in response to the triggering event (e.g., using three-axis accelerometer data rather than single-axis accelerometer data).

In some examples, process 600 can be further modified to reduce power consumption. For example, when an initial determination of a handwashing event by a low-power processor is satisfactory, a handwashing event can be reported without waking the host processor and processing the accelerometer data and/or audio data. In such cases, processing by the host processor to detect the handwashing event again would be redundant. However, when the initial determination of the handwashing event by the low-power processor is insufficient on its own (e.g., insufficient confidence in the accuracy of the result), the host processor can wake and process the accelerometer data and/or audio data. This modification is shown in FIG. 6 at 660. For example, the detection of handwashing event by the low-power processor can include a confidence measure (e.g., between 0 and 1). When the confidence in the detection of a handwashing event at 625 is less than a threshold, process 600 can continue to 630 and wake up the host processor for further processing. When the confidence in the detection of a handwashing event at 625 is greater than the threshold, process 600 can report a handwashing event at 650 and bypass processing by the host processor.

Referring back to processes 500 and 600 illustrated in FIGS. 5 and 6, both processes presume at least partial processing by the low-power processor and the powering up (or powering down) of the host processor based on the detection (or non-detection) of a qualifying handwashing event. In some examples, however, processing similar to processes 500 and 600 can be implemented in a low-power processor (e.g., low-power processor 109) or in a processor (e.g., host processor 108) that consumes more power than the low-power processor. For example, processing accelerometer data and audio data at 615 (e.g., using first accelerometer data processing and using first audio data processing) can trigger or not trigger subsequent processing at 635 (e.g., using second accelerometer data processing and using second audio data processing) on the same low-power processor (e.g., without needing to wake up or power down a second processor).

In some examples, different choices of lower-power, lower-accuracy audio and/or accelerometer models or higher-power, higher-accuracy audio and/or accelerometer models may be used by the lower or higher power/performance processors. In some examples, generally the lowest power audio and/or accelerometer models can operate on the lowest-power processors a higher percentage of the time, and the higher-power, higher-accuracy audio and/or accelerometer models can operate on the higher-power processors a lower percentage of the time to reduce (or minimize) overall power consumption. In some examples, the lower-power, lower-accuracy audio and/or accelerometer models (e.g., by the lower-power processor), can trigger the use or higher-power, higher-accuracy audio and/or accelerometer models (e.g., by the lower-power or higher-power processor) or visa-versa. In some examples higher-power, higher-accuracy audio and/or accelerometer models and/or higher-power processors are used to confirm or overrule a determination of handwashing event by the lower-power, lower-accuracy models. In some examples, audio and/or accelerometer models and processors running these models can be adjusted for the best overall power and experience. In some examples these models or processor configuration changes can be automatically selected (e.g., based on battery level, etc.) or manually selected by a user.

In some examples, the host processor may be powered up or powered down independently of the detection of handwashing events. For example, the host processor may be powered up to perform other processing functions that may use host processor (e.g., touch processing, launching applications, display functionality, etc.). In some such examples, processes 500 and 600 can be modified such that while the host processor is active (and there are sufficient processing resources available at host processor), the processing of acceleration and/or audio data can be performed by the host processor (without using the low-power processor). In some examples, while the host processor is active, the processing can be performed by the host processor according to process 300 or process 400.

In some examples, some processes (e.g., processes 500 and 600) can also be modified based on other considerations. For example, processing power and latency of processing can be traded-off (e.g., as controlled by a power management system). In some examples, processing of acceleration and/or audio data by the low-power processor can be performed (e.g., 510, 615, etc.), but processing by the host processor (e.g., 525, 635) can be deferred until other triggering conditions are met. In such examples, the accelerometer data and/or audio data can be stored for later processing by the host processor (e.g., once the triggering conditions are met). With this modification, increasing the latency of processing to detect the handwashing event can reduce power consumption of the device. Likewise, decreasing the latency of processing to detect the handwashing event can increase power consumption of the device. The triggering conditions to reduce latency can include, for example, battery level above a threshold, charging state (e.g., plugged into AC adapter or charging via wireless charging circuitry), normal power state of the device (not a low-power state or mode), a user request to view handwashing performance or application request to view handwashing performance (e.g., at a specific time of day, such as 5 pm), and/or the activation of the host processor for other functionality (e.g., as described above). The trigger conditions to increase latency can include, for example, battery level falling below a threshold (the same or different than the above battery threshold), non-charging state (removed from wired or wireless charger), a low-power state (or mode) of the device, etc.

In some examples, some processes (e.g., processes 400, 500 or 600) can be modified based on power considerations to simultaneously acquire acceleration and audio data (without triggering audio data collection using an acceleration-based trigger), and/or to acquire higher quality acceleration and/or audio data (without corresponding triggering event (s)), and/or to concurrently processing to detect a qualifying scrubbing event and rinsing event (without sequencing to require detecting a scrubbing event prior to triggering the processing to detect a rinsing event) while power concerns are less critical (e.g., while charging, while battery level is above a threshold, etc.) and to use triggering to acquire and/or process audio data while power concerns are more critical (e.g., not charging, while battery level is below a threshold, etc.).

In addition to considering the latency vs. power trade-off, some of the processes above may be modified to consider a power budget provided for the handwashing detection feature. For example, a portable device (e.g., wearable device 150) may operate using battery power, and the portable device may support numerous features (e.g., media playback, display, etc.) aside from the handwashing detection feature. Accordingly, the handwashing detection feature can be provided with a power budget to provide sufficient power for these other features. In some examples, the mitigation techniques described above can allow for better use of the power budget for the handwashing detection feature. In some examples, however, handwashing detection processes (e.g., the triggers themselves) can be further adjusted based on the available power budget for the feature.

In some examples, the power budget can provide for processing data a maximum number of times for a duration of time. For example, the power budget can allow for a maximum number (e.g., 10, 15), etc. of processing cycles per hour. Once the maximum number is reached, the system can forgo further processing for handwashing detection. In some examples, rather than limiting the maximum number of processing cycles (which could result in missing true positive handwashing events due to too many false positive handwashing events), the requirements for a detecting a qualifying scrubbing event and/or for detecting a qualifying rinsing event (and/or for any other triggers described herein) can be adjusted. For example, as the maximum number of processing cycles is approached for the duration of time, one or more criteria can be heightened for detecting a qualifying scrubbing event (e.g., requiring a longer and/or more vigorous scrub). In some examples, the adjustment can further be based on the number of true positive and false positive events in the duration of time. For example, if each qualifying scrubbing event ultimately is detected as a qualifying handwashing event, the triggers and/or criteria may not be adjusted (or may be adjusted downward to be more sensitive) despite approaching or reaching the maximum number. If each qualifying scrubbing event ultimately is determined to be a non-qualifying handwashing event, the triggers and/or criteria may be adjusted (heightened) to be less sensitive as the maximum number approaches or is reached. In some examples, the adjustment can take into account both false positive and true positive outcomes with the duration of time. The triggers and/or criteria can be adjusted (heightened or lowered) based on the numbers of both false positives and true positives.

In some examples, the adjustment of triggers and/or criteria may also take into account the battery level and/or charging state of the device. For example, while charging or while the battery level is greater than a threshold, the handwashing detection processing can be more sensitive (e.g., without adjusting/heightening triggers), whereas while not charging or while the battery level falls before a threshold, the handwashing detection processing can be adjusted to be less sensitive (e.g., by adjusting/heightening triggers) or the processing can stop.

It should be understood that the above examples are exemplary processes and modifications. More generally, it should be understood that the power consumption mitigations for the acquisition of data and the processing of to detect a handwashing event, as described herein, can vary based on a mode of operation. For example, the mitigations can include one or more of: (1) acquiring audio data in response to an acceleration-based trigger; (2) processing audio data in response to an acceleration-based trigger; (3) processing the audio data (and/or accelerometer data) in a host processor based on low-power processor trigger (or other trigger); (4) increasing a quality of audio and/or accelerometer data based on a trigger; and (5) increasing a quality or size of an audio and/or accelerometer model used for processing based on a trigger. For example, process 400 in FIG. 4 illustrates at least mitigations (1) and (2), process 500 in FIG. 5 illustrates mitigations (1), (2) and (3), and process 600 in FIG. 6 illustrates at least mitigations (3), (4) and (5). In various modes of operations, none, some or all of these mitigations can be applied. Additionally, further mitigations can include adjusting some of the triggers (or qualifying event criteria) to change the sensitivity of the handwashing detection system, and thereby reduce processing/power consuming activity. Whether to apply one or more of the above mitigations can depend on the mode of operation, which can depend on various state variables.

The state variables can include power-related variables. For example, the power-related state variables can include power budget available for the handwashing detection feature, battery level, and/or charging state. For example, (some or all) mitigations can be added and/or trigger(s) adjusted to increase power savings as the power budget for the handwashing detection feature falls, and the mitigations (some or all) can be removed and/or trigger(s) can be adjusted to reduce power savings as the power budget for the handwashing detection feature rises. Mitigations (some or all) can be added and/or trigger(s) adjusted to increase power savings as the battery level for the electronic device detecting handwashing events falls, and the mitigations (some or all) can be removed and/or trigger(s) can be adjusted to reduce power savings as the battery level for the electronic device rises. Mitigations (some or all) can be added and/or trigger(s) adjusted to increase power savings while the electronic device is decoupled from a charger, and the mitigations (some or all) can be removed and/or trigger(s) can be adjusted to reduce power savings while the electronic device charges.

The state variables can also include, in some examples, latency-related variables. For example, a setting can define the latency for reporting handwashing event results. While the setting allows for additional latency in reporting, one or more mitigation(s) can be included to reduce power while still meeting the latency requirements. While the setting does not allow for additional latency in reporting, one or more mitigation(s) can be removed to meet the latency requirements. In some examples, a user or application request can result in a removal of one or more mitigation(s) to reduce latency in responding to the user request.

In some examples, hysteresis can be implemented to avoid high-frequency changing of states. In some examples, the mitigation(s) and/or trigger(s) can be changed between processing cycles to detect a handwashing event. For example, the mitigation(s) and/or trigger(s) can be changed each time the processing returns to the initial processing step for a newly acquired acceleration data sample (e.g., immediately prior to returning to 315, 410, 505, 615).

In some examples, it may be useful to determine an end of a handwashing event. For example, the end of the handwashing event can be used to differentiate between two different handwashing events and/or can be used to limit the number of handwashing events (e.g., for power saving purposes). In some examples, a threshold period of time (e.g., 15 second, 30 seconds, 1 minute, etc.) must pass after detection of a qualifying motion event or qualifying handwashing event (e.g., once a threshold duration of scrubbing is detected and/or once a subsequent rinse is detected) before further motion can trigger processing of further motion data (and/or audio data). In some examples, the threshold period of time can be determined based on a state variable (e.g., shorter duration when there the device has more power or is charging, longer duration when the device has less power, is in a low-power state, etc.).

In some examples, the end of a handwashing event can be determined using a confidence parameter. The confidence parameter can be a probability that the motion data indicates scrubbing (e.g., between 0 and 1). When the confidence is above a threshold (indicative of scrubbing), and then transitions to below a threshold (indicative of the end of scrubbing) for a threshold period of time, the handwashing event can be determined to be concluded. Subsequent motion can trigger processing for detecting a new handwashing event.

In some examples, the accuracy of detecting qualifying handwashing events can be improved by detecting the presence of water or other liquid. For example, a touch sensitive surface of a wearable device (e.g., touch screen 152 of wearable device 150) can be used to detect the presence of water, which may indicate a rinsing event. This information can be used in addition to or instead of detecting rinsing via audio data. For example, the indication of water on the touch screen can increase the confidence that a rinsing took place. For example, the indication of water can increase confidence that the audio data indicative of a rinse is from the wearer rinsing hands (because the water contacting the touchscreen may result from the rinsing), rather than the audio data indicative of another source of running water (e.g., another person washing hands). In some example, the indication of water of the touch-sensitive surface can be used to detect a rinsing event without processing the audio data (e.g., for non-water based hand disinfection or if the audio data is noisy/corrupted/unavailable).

In some examples, the touch sensitive surface (e.g., touch screen 152) can perform two different types capacitive touch scans. A first (guarded) touch scan can detect the presence of objects (e.g., fingers, stylus, etc.) without detecting floating water/liquids. A second (unguarded) touch scan can detect the presence of both objects and floating water/liquids. The difference between the results of the two scans can provide an indication of water/liquid and/or the amount of water/liquid on the surface. In some examples, when the amount of water/liquid is above a threshold (e.g., 25%, 50%, etc.), the amount of water can indicate a qualifying rinsing event and/or can validate or increase the confidence in detection of a qualifying rising event using the audio data.

In some examples, the accuracy of detecting qualifying handwashing events can be improved by differentiating between near-field and far-field audio data. For example, multiple audio sensors (e.g., microphones) within wearable device 150 can be used to differentiate between near-field audio (within a threshold distance of the wearable device) and far-field audio (more than a threshold distance from the wearable device). Near-field audio can include audio indicative of rinsing the hands, whereas far-field audio may be indicative of running water from another source unrelated to rinsing the hands (e.g., from another sink or other water source that is not in close proximity with the wearer of the wearable device). The near-field and/or far-field audio data can be acquired using audio beam forming techniques or audio triangulation techniques.

In some examples, to reduce power consumption, the audio data can be acquired from the near-field only (e.g., using beam forming to acquire near-field audio). In some examples, the audio sensors can acquire both near-field and far-field audio data. In some examples, to reduce power consumption, the near-field audio data can be acquired, and when there is an indication of a running water source in the near-field audio data, the acquisition of far-field audio data can be triggered. The absence of the sound of running water/rinsing in the far-field audio data can then be used to improve confidence in the determination of a qualifying rinsing event based on the near-field audio data. In some examples, the far-field audio detection can be stopped (or not performed) when there is an indication of water on the touch screen (above a threshold amount) because the presence of water may validate or further build confidence in the detection of a qualifying rinsing event.

In some examples, the accuracy of detecting qualifying handwashing events can be improved by using different audio models under different conditions. For example, the audio data corresponding to a hand rinsing event may be different depending on whether an audio sensor (e.g., a microphone) is obstructed. Clothing (e.g., a sleeve or glove), for example, can cover and obstruct the audio sensor. In some examples, the presence (or absence) of an obstruction can be estimated, and can be used to select the audio model from multiple audio models (and/or select the accelerometer model from multiple accelerometer models) that may be customized for higher accuracy of detecting handwashing events given those conditions (e.g., a sleeve audio model may be customized for muted audio, as opposed to a sleeveless audio model).

In some examples, estimation of an obstruction can be based on one or more ambient light sensors. For example, a wearable device 150 can include one or more ambient light sensors (e.g., corresponding to sensors circuitry 211). In some examples, when an object covers the ambient light sensor or when in a low-light environment, the ambient light detected by the ambient light sensor(s) can be below a threshold. In order to differentiate between the former (which may impact the audio data) and the latter (which may not), a differential between two measurements of the ambient light sensor can be used. The display (e.g., touchscreen 152) of the wearable device (or another light source) can be on during one measurement and off during the other measurement. In a low-light environment, the measurements by the ambient light sensors(s) can be similar whether the display is on or off (such that the differential can be zero or within a threshold amount of zero). When the wearable device is covered, however, the measurement by the ambient light sensor(s) while the screen is on and off can be different, due to the light from the display (or another light source, such as an infrared LED) scattering back to the ambient light sensor due to the obstruction, such that the differential can be above a threshold.

In some examples, estimation of an obstruction can be based on a differential between different ambient light sensors. One ambient light sensor can be located in a first portion of the device and one ambient light sensor can be located in a second portion of the device on the opposite side of the device. For example, one ambient light sensor can be disposed on the left side of the device and one ambient light sensor can be disposed on the right side of the device. For a wearable device worn on the left hand, the ambient light being below a threshold for the left side ambient light sensor, but above a threshold for the right side ambient light sensor can be indicative of partial covering of the device by a sleeve (and the differential measurement can have a magnitude above a threshold), whereas in a low-light environment both of the ambient light sensors may detect ambient light below a threshold (and the differential measurement between the two sensors can be approximately zero).

In some examples, estimation of an obstruction can be based on other sensors (in addition to or instead of the ambient light sensor(s)). For example, one or more proximity sensors (e.g., infra-red proximity sensor) or an optical sensor (e.g., camera) can be used to detect proximity of an object (or of a sleeve in particular using a camera). The proximity of an object (within a threshold distance) can be indicative of an object covering the wearable device and/or obstructing the audio sensor. In some examples, the acoustic profile measured by the audio sensor can be used to predict or infer that the audio sensor is covered/obstructed and/or detect the act of covering (or uncovering) of the audio sensor.

Figure 7:
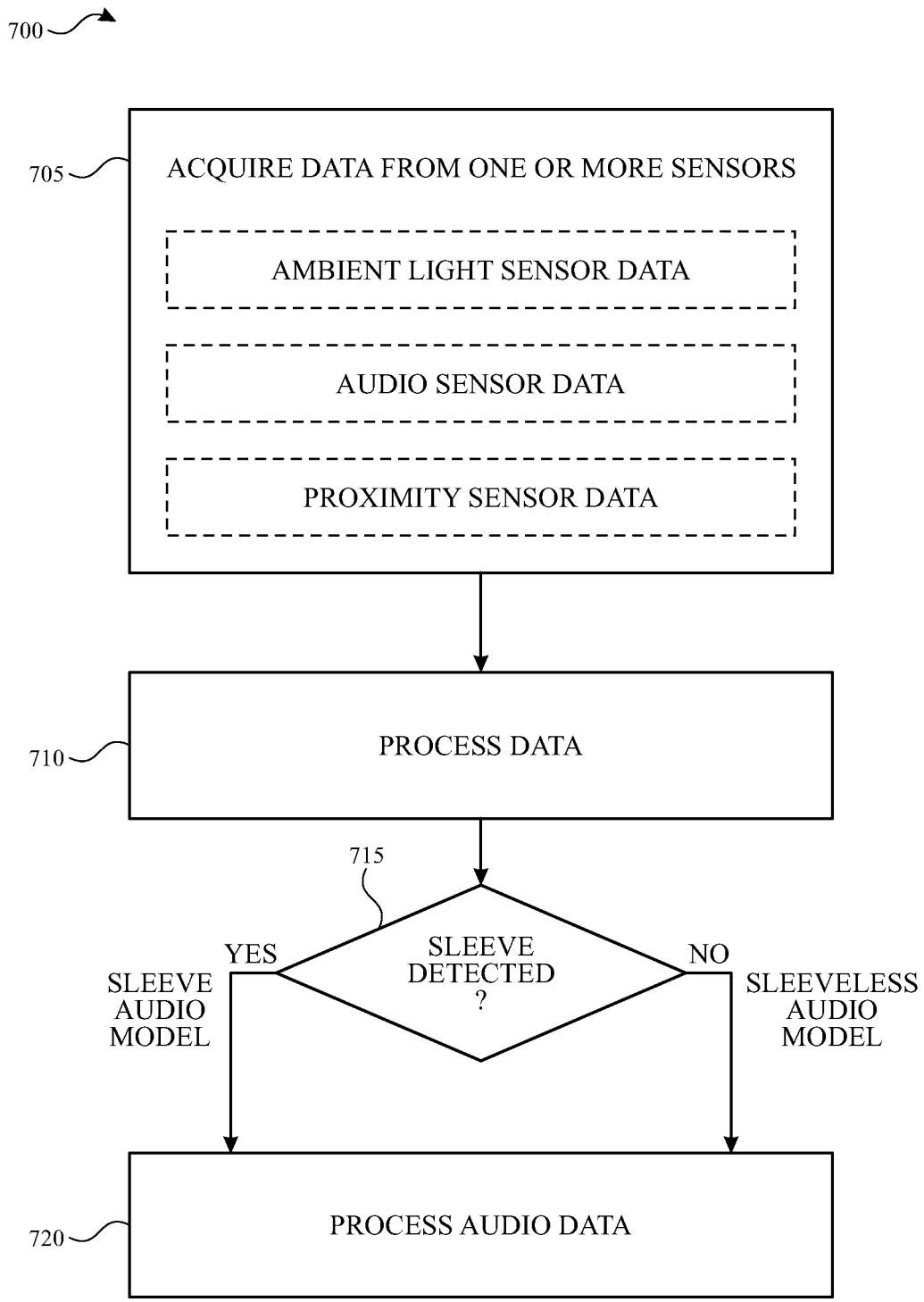
FIG. 7 illustrates an example process for processing audio data in accordance with different audio models according to examples of the disclosure.

FIG. 7 illustrates an example process for processing audio data in accordance with an audio model dependent on whether the audio sensor is obstructed or non-obstructed according to examples of the disclosure. Process 700 can include acquiring data from one or more sensors. For example, as described above, ambient light data from one or more ambient light sensors can be acquired (e.g., with and without the display being on), proximity data from one or more proximity sensors can be acquired, and/or audio data can be acquired at 705. It should be understood that these are examples of possible sensors that can be used for detecting/estimating a sleeve or other object obstructing or covering the audio sensor, but that other sensors can be used. At 710, the data from the one or more sensors can be processed for sleeve detection. The data processing can include computing a differential between ambient light measurements, comparing ambient light measurements/differentials to one or more thresholds, comparing audio data to an audio profile or one or more thresholds, and/or comparing proximity measurements to one or more thresholds. The processing can be used to estimate whether a sleeve (or other obstruction) is detected, at 715. In accordance with detecting a sleeve or other obstruction of the audio sensor, the processing of audio data for handwashing detection (e.g., at 315, 425, 525, 615, 635) can be performed, at 720, using an audio model created for detecting a rinsing event when the audio sensor is covered/obstructed. In accordance with not detecting a sleeve or other obstruction of the audio sensor, the processing of audio data for handwashing detection (e.g., at 315, 425, 525, 615, 635) can be performed, at 720, using an audio model created for detecting a rinsing event when the audio sensor is not covered/obstructed.

Although primarily described as using sleeve detection for determining which audio model to use for processing audio data for handwashing detection, it is understood that sleeve detection can also be used for other purposes. For example, the detection of a sleeve over the display of a wearable device can be used to turn off the display (or decrease its refresh rate) and/or other processes (e.g., touch sensing on a touch screen display, etc.) when a sleeve is detected to reduce power consumption and improve battery life. The display can be turned on (or increase its refresh rate) and/or resume other processes when the sleeve is no longer detected over the display.

Referring back to processes 300, 400, 500 and 600, each process detects a qualifying handwashing event including a qualifying scrubbing event (e.g., detecting inputs the system considers to be scrubbing hands together) and a qualifying rinsing event (e.g., detecting inputs the system considers to be rinsing of the hands with water). However, in some examples, hands may be sanitized, washed or otherwise disinfected without a running-water rinse. For example, hands may be sanitized or disinfected without a rinse using a hand sanitizer gel or the like. These handwashing events may be referred to herein as hand sanitizing events, a sub-class of handwashing events. Alternatively, hands may be washed with soap, and the soap may be removed from the hands using a stationary water supply or the like (e.g., that may not be detected by the above described audio models, if designed to detect the audio of rinsing hands from running-water sources).

In some examples, handwashing events and/or hand sanitizing events can be detected with motion data, and/or with audio data. For motion-only (e.g., motion data without audio) handwashing/sanitizing detection, a qualifying scrubbing event can be detected based on motion data, and can include detecting motion data meeting one or more criteria optionally including a duration criterion, an amplitude criterion, a speed criterion, etc. The one or more criteria can be set to differentiate between motion associated with scrubbing hands together for handwashing/sanitizing from other motion (e.g., lifting a wrist, swinging arms, various exercises, sitting, typing, etc.). Likewise, detecting a qualifying hand sanitizing event based on audio data can include detecting audio data meeting one or more criteria optionally including a duration criterion, an amplitude criterion, a frequency content criterion, etc. The one or more criteria can be set to differentiate between audio associated with scrubbing hands with a hand sanitizing gel from other audio (e.g., environmental sounds, traffic, wind, etc.).

In some examples, the qualifying hand sanitizing event may be detected including a qualifying scrubbing event using motion data and scrubbing-associated audio data (e.g., to detect the sound of scrubbing with soap or gel) rather than rinse-associated audio data. In such examples, processes 300, 400, 500 and 600 can be modified to use the different expected audio models (to detect sounds of hand-sanitizing versus rinsing), and in these cases forgo audio processing for rinse detection (which may be used for detected qualifying hand washing events). In some such examples, the audio data may be collected earlier or in parallel with motion data (e.g., 300, 600) because the audio for hand-sanitizing may occur earlier (while scrubbing, before the gel is absorbed in the skin or evaporates) than the audio associated with rinsing (which may occur after scrubbing with soap). In some examples a larger audio model, larger accelerometer model, and/or larger combined audio/accelerometer model applied to data from audio and/or motion sensors (and optionally models/data from other sensors) can be trained to monitor for multiple different handwashing or sanitizing scenarios.

In some examples, the qualifying handwashing event includes a qualifying scrubbing event using motion data without using audio (e.g., motion-only). In such examples, processes 300, 500, and 600 can be modified to exclude the use of audio models (using one or more accelerometer-based detection stages). In some examples, a first stage (e.g., 510, 615-620) can use accelerometer data to detect initial motion, and then a second stage (e.g., 530, 635-640) can use additional accelerometer data to detect scrubbing with gel or hand sanitizer.

In some examples, the motion-only based handwashing detection and/or a hand sanitizing detection (with or without audio) can use different quality metrics for motion than used for a motion and audio based handwashing detection. The former may require specific types of motion (e.g., a signature of motion), duration of motion (e.g., longer), and/or amplitude of motion (e.g., higher) that may be different than those required for the latter. For example, a gel-based scrubbing may show a different motion signature (e.g., specific scrubbing pattern) in the accelerometer stream than handwashing with soap scrub followed by rinse. In some examples, the specific motion signature can be related to the dispenser for dispensing the gel. In some examples, communication with the hand sanitizer dispenser or geolocation near a hand sanitizer dispense can be used as an input to indicate a higher confidence that the motions detected correspond to a handwashing/sanitizing event.

It should be understood that in some examples, the wearable device can perform multiple processes for detection of individual events. For example, the wearable device can use motion and audio data to detect qualifying handwashing events with a qualifying scrubbing event and a qualifying rinsing event. The wearable device can also use motion and/or audio to detect hand sanitizing events. Thus the wearable device can detect and track alternate forms of hand washing/sanitizing.

In some examples, detecting handwashing events (both qualifying and non-qualifying) can be monitored and/or used to provide feedback. For example, feedback can encourage a user to wash hands longer or more vigorously depending on the duration and vigor of past or current handwashing. In some examples, the feedback can indicate a "poor" hand wash (too short and/or not enough vigor to be a qualifying handwashing event), and optionally can prompt to re-wash hands. In some examples, a "moderate" hand wash (moderate duration and/or vigor) can result in feedback providing encouragement to perform a better wash the next time. In some examples, a "good" hand wash (full duration and/or vigor for qualifying handwashing event) can result in feedback applauding the user's hand washing performance.

In some examples, the feedback can include a countdown timer (visual and/or audio and/or haptic) to encourage a user to scrub hands for a threshold period of time (e.g., 20 seconds). In some examples, the countdown timer can be triggered internally based on observing a sub-scrubbing event in the motion data (e.g., that may indicate a first confidence that the motion is from scrubbing), but the countdown timer can be presented to the user later after a higher confidence is achieved that the motion data truly corresponds to scrubbing. In some examples, the feedback can include prompts to improve the duration (scrub longer) and/or quality of scrubbing hands (e.g., scrub harder or scrub specific parts of the hands). In some examples, the feedback can include instructions to wash specific parts of the hand (e.g., fingernails, back-of-hand, etc.). The scrubbing motions for cleaning the fingernails and/or back-of-hand, etc. may be detected based on sub-motions in the motion data (accelerometer stream). In some examples, a prompt to scrub longer can be made if scrubbing stops/pauses for a threshold duration before the target duration of a qualifying handwashing it met. In some examples, a prompt for more vigor (e.g., when insufficient vigor is detected based on accelerometer stream) can be made if the scrubbing is below a vigor target for a threshold amount of time. In some examples, a prompt to wash specific parts of the hand can be made if the user pauses scrubbing for a threshold period of time without washing these specific parts.

In some examples, the monitoring of handwashing can include information about qualifying and/or non-qualifying handwashing event, the duration of the event (e.g., including scrub time), and the quality of the event. The information can also include a time stamp, a comparison of the duration to a target duration, and information about the duration and/or vigor of the scrubbing. In some examples, handwashing events can be separately monitored from hand sanitizing events. In some examples, parents can monitor information about handwashing of children and hospitals can monitor handwashing of medical workers, etc.

In some examples the user's particular style of handwashing may result in inadequate triggering or other activities may result in erroneous triggering of the event notification. In some examples, the user can provide feedback (e.g., through one or more menus indicating whether a handwashing or hand sanitizing event did or did not occur) that will allow for further refinement of the model(s) that are better adapted to detecting these events for the particular user.

In some examples, the requirements for a qualifying handwashing event (e.g., triggers, thresholds, metrics) and handwashing reminders can be specific to a user and/or location. For example, different requirements/reminders can be used for children than for adults (or different models can be used for different aged children), and different requirements/reminders can be used for medical workers or food preparation workers than for other workers, and/or different requirements/reminders can be used for a school or hospital than for other places. The requirements generally can be higher for adults compared with children (e.g., where habit-making may be more emphasized than quality) and for medical workers compared with other workers. The requirements can be higher and/or the handwashing reminders more significant and when leaving locations with relatively high contamination risks (e.g., a bathroom, playground etc.) and/or entering locations with relatively high cleanliness requirements (e.g., hospital, patient room, kitchen, etc.). In some examples, the heightened requirements and/or handwashing reminders may be limited to specific transitions between high-contamination risk locations to high-cleanliness locations (e.g., transitioning from a bathroom and a kitchen, or from an infected patient's room to immunodeficient patient's room, or from a playground and a cafeteria), but not between other transitions (e.g., transitioning between a bathroom and a bedroom, between a living room and a kitchen, etc.). In some examples, the heightened requirements may be linked to a specific person and location. For example, heightened requirements can be used for a doctor while in the hospital than would be used for a doctor outside the hospital or a visitor in the hospital.

In some examples, the alerts related to location can be unscheduled for a period of time if the user has washed their hands and the event has been logged within a specific period of time after arrival at the location, and in this fashion the user is reinforced to remember themselves and avoid the alert.

In some examples, a specific machine learning model can be generated that outputs a handwashing score based on motion and/or audio inputs. The score may be represent a relative effectiveness of certain handwashing techniques, and the score may correlate with a reduction in germ-count. For example, the inputs to the machine learning model can include motion (e.g., accelerometer) and/or audio data from the motion and/or audio sensors as inputs to the model, and the output of the machine learning model can be a score. The score may correlate with an amount of germ-count reduction or an indication that a threshold amount of germ-count reduction is achieved. For training the model, the inputs to the machine learning model can include training data of a germ-count before and after some motion/audio indicative of handwashing. The machine learning model can then learn a model that attempts to correlate the motion and/or audio inputs to germ-count reduction that was measured or derived for the training data. In some such examples, timers described herein can be supplemented by the score. For example, the handwashing can be qualifying handwashing event after washing for the duration of the timer and/or after achieving the desired score (e.g., possibly correlated with a desired germ-count reduction). In some examples, achieving the desired score can cause the timer to end early or otherwise shorten the duration of the timer (e.g., reducing the duration of the timer). In some examples, failure to achieve the desired score can cause the timer to be extended. In some such examples, the timers described herein can be supplanted by a score. For example, instead of using a timer for determining the quality of the handwashing event and/or using a timer for feedback to the user, the handwashing can be qualifying after achieving the desired score as measured or derived by the machine learning model.

The requirements for a qualifying handwashing event and handwashing reminders may also be different in response to detecting a germ/contamination-based event. For example, a toilet flush or cough/sneeze can be detected using the audio data and can be used to trigger handwashing reminder and/or heightened handwashing requirements. In some examples, the accelerometer data can be used to detect the source of the cough. For example, a high frequency body movement (resonance, echo) may indicate that the cough/sneeze was by the wearer (e.g., of wearable device 150) rather than by another. The heightened handwashing requirements and/or reminders may be applied when the user coughs/sneezes, but not when another person coughs/sneezes.

In some examples, the audio data can be used to differentiate between a cough and a sneeze. In some examples, the audio data may be used to differentiate between wet cough and dry cough. In some examples, to detect cough/sneeze, the audio sensors (e.g., microphone) may need to remain active (rather than be triggered by motion after the fact). In some examples, the audio data can be processed to detect cough/sneeze, and when a cough/sneeze is detected, the motion stream (from a data buffer) can be used to confirm source (e.g., trigger source detection based on detection of cough/sneeze). In some examples, the device can track cough/sneezes over time to measure effectiveness of medical treatment, suggest doctor visit, etc. (based on duration, frequency, or change in cough/sneeze events over time).

In some examples, the handwashing reminder can be triggered to encourage washing. In some examples, the handwashing reminder can be triggered when a timeout occurs without a detected handwashing event (e.g., after a threshold period of time after a germ-based event is detected, after a threshold period of time after entering and/or leaving specific locations, etc.). This latter type of reminder may be less intrusive as the user is given an opportunity to remember to wash hands without a reminder.

The requirements for qualifying handwashing events can include a threshold time between handwashing events and/or a number of events per hour. In some examples, germ-based events and/or location-based events (e.g., entering and/or leaving specific locations) can require more frequent handwashing than typically anticipated for the sensor (and more than the baseline power budget allotted to the sensor), and thus these triggers can reduce the threshold time between handwashing events or increase the number of allowed events per hour. The requirements for qualifying handwashing events can include metrics such as target duration of handwashing, target vigor of handwashing, etc. In some examples, the latency of processing/feedback may change as well. For example, handwashing processing and/or feedback may be presented with reduced latency after a germ-based event and/or when entering and/or leaving specific locations, whereas handwashing processing and/or feedback may be delayed without these additional triggers. Additionally or alternatively, the latency can be different based on different users (e.g., handwashing processing and/or feedback may be presented with reduced latency for a doctor or food preparer than for a typical adult).

As discussed above, aspects in of the present technology include the gathering and use of physiological information. The technology may be implemented along with technologies that involve gathering personal data that relates to the user's health and/or uniquely identifies or can be used to contact or locate a specific person. Such personal data can include demographic data, date of birth, location-based data, telephone numbers, email addresses, home addresses, and data or records relating to a user's health or level of fitness (e.g., vital signs measurements, medication information, exercise information, etc.).

The present disclosure recognizes that a user's personal data, including physiological information, such as data generated and used by the present technology, can be used to the benefit of users. For example, a user's heart rate or ECG may allow a user to track or otherwise gain insights about their health or fitness levels. As another example, detecting handwashing events can be useful to track information about preventative health practices.

The present disclosure contemplates that the entities responsible for the collection, analysis, disclosure, transfer, storage, or other use of such personal data will comply with well-established privacy policies and/or privacy practices. In particular, such entities should implement and consistently use privacy policies and practices that are generally recognized as meeting or exceeding industry or governmental requirements for maintaining personal information data private and secure. Such policies should be easily accessible by users, and should be updated as the collection and/or use of data changes. Personal information from users should be collected for legitimate and reasonable uses of the entity and not shared or sold outside of those legitimate uses. Further, such collection/sharing should require receipt of the informed consent of the users. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. The policies and practices may be adapted depending on the geographic region and/or the particular type and nature of personal data being collected and used.

Despite the foregoing, the present disclosure also contemplates embodiments in which users selectively block the collection of, use of, or access to, personal data, including physiological information. For example, a user may be able to disable hardware and/or software elements that collect physiological information. Further, the present disclosure contemplates that hardware and/or software elements can be provided to prevent or block access to personal data that has already been collected. Specifically, users can select to remove, disable, or restrict access to certain health-related applications collecting users' personal health or fitness data Therefore, according to the above, some examples of the disclosure are directed to a wearable device (or a system including at least one wearable device). The wearable device can comprise an audio sensor configured to acquire audio data; a motion sensor (disposed in a wearable device of the system) configured to acquire motion data; and processing circuitry programmed to detect a qualifying handwashing event using the audio data and the motion data. Additionally or alternatively to one or more of the examples disclosed above, in some examples, the processing circuitry can be further programmed to: detect, using the motion data, a qualifying motion event; and in response to detecting the qualifying motion event, trigger acquisition of the audio data by the audio sensor. Additionally or alternatively to one or more of the examples disclosed above, in some examples, detecting the qualifying handwashing event using the audio data and the motion data can comprise detecting a qualifying scrubbing event using the motion data and detecting a qualifying rinsing event using the audio data. Additionally or alternatively to one or more of the examples disclosed above, in some examples, detecting the qualifying handwashing event can include detecting the qualifying rinsing event within a threshold period of time of detecting the qualifying scrubbing event. Additionally or alternatively to one or more of the examples disclosed above, in some examples, the processing circuitry can include a first processor and a second processor. The first processor can consume less power during operation than the second processor. Additionally or alternatively to one or more of the examples disclosed above, in some examples, detecting the qualifying handwashing event can include the first processor detecting a triggering condition. The processing circuitry can be further programmed to: in response to the first processor detecting the triggering condition, trigger processing by the second processor. Additionally or alternatively to one or more of the examples disclosed above, in some examples, the first processor can be further programmed to wake up the second processor in response to the triggering condition. Additionally or alternatively to one or more of the examples disclosed above, in some examples, the triggering condition can include a qualifying motion event detected using the motion data. Additionally or alternatively to one or more of the examples disclosed above, in some examples, the triggering condition can include both a qualifying motion event detected using the motion data and a qualifying audio event detected using the audio data. Additionally or alternatively to one or more of the examples disclosed above, in some examples, the triggering condition can include detecting the qualifying handwashing event with a confidence level less than a threshold confidence level. Additionally or alternatively to one or more of the examples disclosed above, in some examples, the processing by the second processor can include detecting a qualifying rinsing event using the audio data. Additionally or alternatively to one or more of the examples disclosed above, in some examples, the processing by the second processor can include detecting the qualifying handwashing event using the audio data. Additionally or alternatively to one or more of the examples disclosed above, in some examples, the processing by the second processor can include detecting the qualifying handwashing event using the audio data and motion data. Additionally or alternatively to one or more of the examples disclosed above, in some examples, the first processor detecting the triggering condition can include detecting a first qualifying audio event using a first machine learning audio model applied to the audio data, and the processing by the second processor can include detecting a second qualifying audio event using a second machine learning model applied to the audio data, the second machine learning model different than the first machine learning model. Additionally or alternatively to one or more of the examples disclosed above, in some examples, the second machine learning model can be of a higher quality or a greater size than the first machine learning model. Additionally or alternatively to one or more of the examples disclosed above, in some examples, the first processor detecting the triggering condition can include detecting a first qualifying motion event using a first machine learning motion model applied to the motion data, and the processing by the second processor can include detecting a second qualifying motion event using a second machine learning model applied to the motion data, the second machine learning model different than the first machine learning model. Additionally or alternatively to one or more of the examples disclosed above, in some examples, the second machine learning model can of a higher quality or a greater size than the first machine learning model. Additionally or alternatively to one or more of the examples disclosed above, in some examples, the audio data can include first audio data and second audio data. The second audio data can be higher quality than the first audio data. Additionally or alternatively to one or more of the examples disclosed above, in some examples, the motion data can include first motion data and second motion data. The second motion data can be higher quality than the first motion data. Additionally or alternatively to one or more of the examples disclosed above, in some examples, detecting the qualifying event can include detecting a triggering condition. The processing circuitry can be further programmed to: in response to detecting the triggering condition, trigger processing by the second processor. Additionally or alternatively to one or more of the examples disclosed above, in some examples, the triggering condition can include the second processor waking up. Additionally or alternatively to one or more of the examples disclosed above, in some examples, the triggering condition can include detecting that the device is charging or detecting a battery level above a threshold. Additionally or alternatively to one or more of the examples disclosed above, in some examples, the triggering condition can change dynamically based a power margin of the device for detecting the qualifying event.

Some examples of the disclosure are directed to a method. The method can comprise: at a wearable device including an audio sensor configured to acquire audio data and a motion sensor configured to acquire motion data: detecting a qualifying handwashing event using the audio data and the motion data. Additionally or alternatively to one or more of the examples disclosed above, in some examples, the method can further comprise: detecting, using the motion data, a qualifying motion event; and in response to detecting the qualifying motion event, triggering acquisition of the audio data by the audio sensor. Additionally or alternatively to one or more of the examples disclosed above, in some examples, detecting the qualifying event using the audio data and the motion data can comprise detecting a qualifying scrubbing event using the motion data and detecting a qualifying rinsing event using the audio data. Additionally or alternatively to one or more of the examples disclosed above, in some examples, detecting the qualifying event can include detecting the qualifying rinsing event within a threshold period of time of detecting the qualifying scrubbing event. Additionally or alternatively to one or more of the examples disclosed above, in some examples, the wearable device can include processing circuitry including a first processor and a second processor. The first processor can consume less power during operation than the second processor. Additionally or alternatively to one or more of the examples disclosed above, in some examples, detecting the qualifying event can include the first processor detecting a triggering condition. The method can further comprise: in response to the first processor detecting the triggering condition, triggering processing by the second processor. Additionally or alternatively to one or more of the examples disclosed above, in some examples, the method can further comprise: the first processor waking up the second processor in response to the triggering condition. Additionally or alternatively to one or more of the examples disclosed above, in some examples, the triggering condition can include a qualifying motion event detected using the motion data. Additionally or alternatively to one or more of the examples disclosed above, in some examples, the triggering condition can include both a qualifying motion event detected using the motion data and a qualifying audio event detected using the audio data. Additionally or alternatively to one or more of the examples disclosed above, in some examples, the triggering condition can include detecting the qualifying event with a confidence level less than a threshold confidence level. Additionally or alternatively to one or more of the examples disclosed above, in some examples, the processing by the second processor can include detecting a qualifying rinsing event using the audio data. Additionally or alternatively to one or more of the examples disclosed above, in some examples, the processing by the second processor can include detecting the qualifying event using the audio data. Additionally or alternatively to one or more of the examples disclosed above, in some examples, the processing by the second processor can include detecting the qualifying event using the audio data and motion data. Additionally or alternatively to one or more of the examples disclosed above, in some examples, the first processor detecting the triggering condition can include detecting a first qualifying audio event using a first machine learning audio model applied to the audio data, and the processing by the second processor can include detecting a second qualifying audio event using a second machine learning model applied to the audio data, the second machine learning model different than the first machine learning model. Additionally or alternatively to one or more of the examples disclosed above, in some examples, the second machine learning model can be of a higher quality or a greater size than the first machine learning model. Additionally or alternatively to one or more of the examples disclosed above, in some examples, the first processor detecting the triggering condition can include detecting a first qualifying motion event using a first machine learning motion model applied to the motion data, and the processing by the second processor can include detecting a second qualifying motion event using a second machine learning model applied to the motion data, the second machine learning model different than the first machine learning model. Additionally or alternatively to one or more of the examples disclosed above, in some examples, the second machine learning model can be of a higher quality or a greater size than the first machine learning model. Additionally or alternatively to one or more of the examples disclosed above, in some examples, the audio data can include first audio data and second audio data. The second audio data can be higher quality than the first audio data. Additionally or alternatively to one or more of the examples disclosed above, in some examples, the motion data can include first motion data and second motion data. The second motion data can be higher quality than the first motion data. Additionally or alternatively to one or more of the examples disclosed above, in some examples, detecting the qualifying event can include detecting a triggering condition, and the method can further comprise: in response to detecting the triggering condition, triggering processing by the second processor. Additionally or alternatively to one or more of the examples disclosed above, in some examples, the triggering condition can include the second processor waking up. Additionally or alternatively to one or more of the examples disclosed above, in some examples, the triggering condition can include detecting that the device is charging or detecting a battery level above a threshold. Additionally or alternatively to one or more of the examples disclosed above, in some examples, the triggering condition can change dynamically based a power margin of the device for detecting the qualifying event.

Some examples of the disclosure are directed to a non-transitory computer readable storage medium. The non-transitory computer readable storage medium can store instructions, which when executed by one or more processing circuits of a wearable device including an audio sensor configured to acquire audio data and a motion sensor configured to acquire motion data, cause the one or more processing circuits to perform any of the above methods.

Some examples of the disclosure are directed to a system comprise an audio sensor configured to acquire audio data; a motion sensor (disposed in a wearable device of the system) configured to acquire motion data; and processing circuitry programmed to detect a qualifying handwashing event using the audio data and the motion data.

Some examples of the disclosure are directed to a wearable device. The wearable device can comprise a motion sensor and processing circuitry. The motion sensor can be configured to acquire motion data. The processing circuitry can be programmed to detect a qualifying handwashing even or a qualifying hand sanitizing event using the motion data. Additionally or alternatively to one or more of the examples disclosed above, in some examples, the wearable device further comprises an audio sensor configured to acquire audio data. The processing circuitry can be further programmed to detect the qualifying handwashing event or the qualifying hand sanitizing event using the motion data and the audio data. Additionally or alternatively to one or more of the examples disclosed above, in some examples, the processing circuitry can be further programmed to: in accordance with a determination that the audio sensor is obstructed, processing the audio data using a first machine learning audio model for an obstructed audio sensor applied to the audio data; and in accordance a determination that the audio sensor is unobstructed, processing the audio data using a second machine learning audio model for an unobstructed audio sensor applied to the audio data. Additionally or alternatively to one or more of the examples disclosed above, in some examples, the wearable device can further comprise one or more ambient light sensors. The determination that the audio sensor is obstructed or unobstructed can be based on a differential measurement from the one or more ambient light sensors (e.g., with an active optical signal during one measurement from a light source such as the screen backlight or an infrared source). Additionally or alternatively to one or more of the examples disclosed above, in some examples, the wearable device can further comprise one or more infrared proximity sensors.

Although examples of this disclosure have been fully described with reference to the accompanying drawings, it is to be noted that various changes and modifications will become apparent to those skilled in the art. Such changes and modifications are to be understood as being included within the scope of examples of this disclosure as defined by the appended claims.

The invention claimed is:

1. A wearable device comprising: a motion sensor configured to acquire first motion data and second motion data; and
  processing circuitry programmed to detect, using the first motion data, a qualifying motion event, wherein detecting the qualifying motion event includes using one or more first quality metrics to detect the qualifying motion event; and
  in response to detecting the qualifying motion event, trigger processing of the second motion data by the motion sensor to detect a qualifying handwashing event using the first motion data and the second motion data, wherein detecting the qualifying handwashing event includes using one or more second quality metrics, different from the one or more first quality metrics, to detect the qualifying handwashing event.

2. The wearable device of claim 1, wherein the processing circuitry includes a first processor and a second processor, the first processor is programmed to trigger operation by the second processor, and wherein the first processor consumes less power during operation than the second processor.

3. The wearable device of claim 2, wherein operating by the second processor includes detecting a qualifying scrubbing event using audio data.

4. The wearable device of claim 2, wherein detecting the qualifying motion event includes the first processor detecting a triggering condition, and wherein the processing circuitry is further programmed to:
   in response to the first processor detecting the triggering condition:
      wake up the second processor; and
      trigger processing by the second processor.

5. The wearable device of claim 1, wherein the processing circuitry is further programmed to:
   in response to detecting the qualifying motion event, trigger acquisition of audio data by an audio sensor, wherein the one or more second quality metrics are based on the audio data.

6. The wearable device of claim 5, wherein the one or more second quality metrics include a duration criterion, an amplitude criterion, or a frequency criterion.

7. The wearable device of claim 1, wherein the one or more first quality metrics include a type of motion, a duration of the motion, or an amplitude of the motion.

8. The wearable device of claim 1, wherein the one or more first quality metrics are based on a user of the wearable device or a location of the wearable device.

9. A non-transitory computer readable storage medium storing instructions, which when executed by one or more processing circuits of a wearable device including a motion sensor configured to acquire first motion data and second motion data, cause the one or more processing circuits to:
   detect, using the first motion data, a qualifying motion event, wherein detecting the qualifying motion event includes using one or more first quality metrics to detect the qualifying motion event; and
   in response to detecting the qualifying motion event, cause the one or more processing circuits to detect, using the first motion data and the second motion data, a qualifying handwashing event, wherein detecting the qualifying handwashing event includes using one or more second quality metrics, different from the one or more first quality metrics, to detect the qualifying handwashing event.

10. The non-transitory computer readable storage medium of claim 9, wherein the one or more processing circuits includes a first processor and a second processor, the first processor is programmed to trigger operation by the second processor, and wherein the first processor consumes less power during operation than the second processor.

11. The non-transitory computer readable storage medium of claim 10, wherein operating by the second processor includes detecting a qualifying scrubbing event using audio data.

12. The non-transitory computer readable storage medium of claim 10, wherein detecting the qualifying motion event includes the first processor detecting a triggering condition, and wherein the instructions, when executed by the one or more processing circuits, cause the one or more processing circuits to:
   in response to the first processor detecting the triggering condition:
      wake up the second processor; and
      trigger processing by the second processor.

13. The non-transitory computer readable storage medium of claim 9, wherein the instructions, when executed by the one or more processing circuits, cause the one or more processing circuits to:
   in response to detecting the qualifying motion event, trigger acquisition of audio data by an audio sensor, wherein the one or more second quality metrics are based on the audio data.

14. The non-transitory computer readable storage medium of claim 13, wherein the one or more second quality metrics include a duration criterion, an amplitude criterion, or a frequency criterion.

15. The non-transitory computer readable storage medium of claim 9, wherein the one or more first quality metrics include a type of motion, a duration of the motion, or an amplitude of the motion.

16. The non-transitory computer readable storage medium of claim 9, wherein the one or more first quality metrics are based on a user of the wearable device or a location of the wearable device.

17. A method comprising:
   at a wearable device including a motion sensor configured to acquire first motion data and second motion data and processing circuitry:
   detecting a qualifying motion event using the first motion data, wherein detecting the qualifying motion event includes using one or more first quality metrics to detect the qualifying motion event; and
   in response to detecting the qualifying motion event, triggering processing of the second motion data by the motion sensor to detect a qualifying handwashing event using the first motion data and the second motion data, wherein detecting the qualifying handwashing event includes using one or more second quality metrics, different from the one or more first quality metrics, to detect the qualifying handwashing event.

18. The method of claim 17, wherein the one or more first quality metrics include a type of motion, a duration of the motion, or an amplitude of the motion.

19. The method of claim 17, wherein the one or more first quality metrics are based on a user of the wearable device or a location of the wearable device.

20. The method of claim 17, further comprising:
   in response to detecting the qualifying motion event, triggering acquisition of audio data by an audio sensor, wherein the one or more second quality metrics are based on the audio data.

* * * * *